United States Patent
Hayashida et al.

(10) Patent No.: US 11,298,177 B2
(45) Date of Patent: Apr. 12, 2022

(54) ENERGY SOURCE APPARATUS

(71) Applicant: Olympus Corporation, Hachioji (JP)

(72) Inventors: Tsuyoshi Hayashida, Hachioji (JP);
Sadayoshi Takami, Hachioji (JP);
Toshifumi Katsuragi, Hachioji (JP);
Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 301 days.

(21) Appl. No.: 16/568,669

(22) Filed: Sep. 12, 2019

(65) Prior Publication Data
US 2020/0000509 A1    Jan. 2, 2020

Related U.S. Application Data

(63) Continuation of application No. PCT/JP2017/010456, filed on Mar. 15, 2017.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61B 2018/0016* (2013.01); *A61B 2018/126* (2013.01); *C23C 14/0063* (2013.01)

(58) Field of Classification Search
CPC ....... A61B 18/085; A61B 18/10; A61B 18/12; A61B 18/1206; A61B 18/14;
(Continued)

(56) References Cited

U.S. PATENT DOCUMENTS 5,403,312 A    4/1995  Yates et al.
8,500,735 B2 *  8/2013  Tanaka ............... A61B 18/1442
                                                      606/51
(Continued)

FOREIGN PATENT DOCUMENTS

JP          8196543         8/1996
JP        2009247893       10/2009
(Continued)

OTHER PUBLICATIONS

International Search Report and Written Opinion from corresponding International Application No. PCT/JP2017/010456, dated Jun. 13, 2017.

*Primary Examiner* — Michael F Peffley
(74) *Attorney, Agent, or Firm* — Oliff PLC

(57) ABSTRACT

A treatment system includes a treatment tool and an energy source apparatus. The treatment tool includes a heater and bipolar electrodes to grip a treatment target. The energy source apparatus supplies electrical energy to the treatment tool. A processor controls the output to the bipolar electrodes and the heater. The processor causes a high-frequency electric power to be output to the bipolar electrodes and detects a parameter that varies depending on tissue volume of the treatment target. The processor sets a target value related to an output control process for controlling the output to the heater. The processor controls the output to the heater so as to modify the treatment target with the heat of the heater. The processor increases the output and temperature to the heater until at least a predetermined point of time after starting the output control process for controlling the output to the heater.

14 Claims, 10 Drawing Sheets

(51) Int. Cl.
   *A61B 18/00* (2006.01)
   *C23C 14/00* (2006.01)

(58) Field of Classification Search
   CPC ........ A61B 18/1445; A61B 2018/0016; A61B 2018/00404; A61B 2018/00589; A61B 2018/0063; A61B 2018/00642; A61B 2018/00673; A61B 2018/00702; A61B 2018/00761; A61B 2018/00791; A61B 2018/00875; A61B 2018/00994; A61B 2018/126; C23C 14/0063
   See application file for complete search history.

(56) References Cited

U.S. PATENT DOCUMENTS

| | | | |
|---|---|---|---|
| 9,642,665 B2 * | 5/2017 | Weinberg | A61B 18/1233 |
| 10,034,703 B2 * | 7/2018 | Takashino | A61B 18/04 |
| 10,098,688 B2 * | 10/2018 | Takashino | A61B 18/1442 |
| 10,441,341 B2 * | 10/2019 | Honda | A61B 18/085 |
| 2009/0248002 A1 | 10/2009 | Takashino et al. | |
| 2012/0136354 A1 | 5/2012 | Rupp | |
| 2013/0338656 A1 | 12/2013 | Irisawa et al. | |

FOREIGN PATENT DOCUMENTS

| | | |
|---|---|---|
| JP | 2012115669 | 6/2012 |
| WO | 2013088891 | 6/2013 |

\* cited by examiner

ENERGY SOURCE APPARATUS

CROSS-REFERENCE TO RELATED APPLICATION

This application is a continuation application of PCT Application No. PCT/JP2017/010456 filed on Mar. 15, 2017, which is hereby incorporated by reference in its entirety.

TECHNICAL FIELD

The disclosed technology relates generally to an energy source apparatus, and more particularly, some embodiments relate to an energy source apparatus for use with a treatment tool having bipolar electrodes and a heater.

DESCRIPTION OF THE RELATED ART

US Patent Application 2009/0248002A1 discloses a treatment tool capable of gripping a treatment target such as a biotissue or the like between a pair of grippers and an energy source apparatus for supplying the treatment tool with electric energy. In the treatment tool, each of the grippers includes an electrode and one of the grippers includes a heater. The energy source apparatus outputs high-frequency electric power to the electrodes, i.e., bipolar electrodes, and outputs heater electric power to the heater. Consequently, a high-frequency current flows between the electrodes through the gripped treatment target and heat generated by the heater is applied to the gripped treatment target. In other words, both the high-frequency current and the heater heat are applied to the treatment target.

As disclosed in the US Patent Application US2009/0248002A1, a treatment using a treatment tool that applies both a high-frequency current and heater heat to a treatment target may modify the treatment target by applying the high-frequency current, the heater heat, etc. thereto, sealing or coagulating the treatment target. In this case, it is required to prevent a lateral thermal spread in which heat caused by the high-frequency current spreads outwardly in the widthwise directions of the grippers from the gripped treatment target in the biotissue. It is thus required to control the output from a heater power supply to the heater and the output from a high-frequency power supply to the electrodes depending on the state of the treatment target in a manner to prevent the lateral thermal spread.

BRIEF SUMMARY OF EMBODIMENTS

The disclosed technology has been made in view of the foregoing.

One aspect of the disclosed technology is directed to an energy source apparatus for use with a treatment tool having a heater and bipolar electrodes. The energy source apparatus includes an energy output source that outputs high-frequency electric power to the bipolar electrodes so as to cause a high-frequency current to flow through a treatment target between the bipolar electrodes and outputs heater electric power to the heater so as to cause the heater to generate heat. A processor controls the output to the bipolar electrodes and the output to the heater. The processor causes the high-frequency electric power to be output to the bipolar electrodes and detects a parameter that varies depending on tissue volume of the treatment target. The parameter is related to (i) impedance of the treatment target and/or (ii) the output to the bipolar electrodes. The processor sets a target value based on the detected parameter and the target value is related to an output control process for controlling the output to the heater. The processor controls the output to the heater based on the target value so as to modify the treatment target with the heat of the heater. With respect to a smaller tissue volume, the processor increases the output to the heater and increases a temperature of the heater until at least a predetermined point of time after starting the output control process for controlling the output to the heater based on the target value.

Another aspect of the disclosed technology is directed to a treatment system having a treatment tool. The treatment tool includes a heater and bipolar electrodes to grip a treatment target. An energy source apparatus is used to supply electrical energy to the treatment tool. The energy output source outputs high-frequency electric power to the bipolar electrodes so as to cause a high-frequency current to flow through a treatment target between the bipolar electrodes and outputs heater electric power to the heater so as to cause the heater to generate heat. A processor controls the output to the respective bipolar electrodes and the heater. The processor causes the high-frequency electric power to be output to the bipolar electrodes and detects a parameter that varies depending on tissue volume of the treatment target. The parameter is related to (i) impedance of the treatment target and/or (ii) the output to the bipolar electrodes. The processor sets a target value based on the detected parameter. The target value is related to an output control process for controlling the output to the heater. The processor controls the output to the heater based on the target value so as to modify the treatment target with the heat of the heater and with respect to a smaller tissue volume, the processor increases the output to the heater and increases a temperature of the heater until at least a predetermined point of time after starting the output control process for controlling the output to the heater based on the target value.

A further aspect of the disclosed technology is directed to a method of operating a treatment system having a treatment tool. The treatment tool includes a heater and bipolar electrodes to grip a treatment target and an energy source apparatus used to supply electrical energy to the treatment tool. The energy output source outputs high-frequency electric power to the bipolar electrodes so as to cause a high-frequency current to flow through a treatment target between the bipolar electrodes and outputs heater electric power to the heater so as to cause the heater to generate heat. The energy source apparatus includes at least one processor to control the output to the bipolar electrodes and the heater, respectively. The at least one processor is causing the high-frequency electric power to be output to the bipolar electrodes and detecting a parameter that varies depending on tissue volume of the treatment target. The parameter is related to (i) impedance of the treatment target and/or (ii) the output to the bipolar electrodes. The processor is setting a target value based on the detected parameter, the target value is related to an output control process for controlling the output to the heater. The processor is controlling the output to the heater based on the target value so as to modify the treatment target with the heat of the heater. With respect to a smaller tissue volume, the processor is increasing the output to the heater and is increasing a temperature of the heater until at least a predetermined point of time after starting the output control process for controlling the output to the heater based on the target value.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the present disclosure to provide an energy source apparatus which appropriately controls the output from a heater power supply and the output from a high-frequency power supply based on the state of a treatment target to effectively prevent a lateral thermal spread from the treatment target in a biotissue.

There is provided in accordance with an aspect of the present disclosure an energy source apparatus used with a treatment tool at a time of using the treatment tool including an end effector capable of gripping a treatment target between a pair of grippers, the end effector including a heater and bipolar electrodes, the energy source apparatus including: an energy output source that outputs high-frequency electric power to the bipolar electrodes thereby to cause a high-frequency current to flow through a treatment target between the bipolar electrodes, and outputs heater electric power to the heater thereby to cause the heater to generate heat; and a processor that controls the output to the bipolar electrodes and the output to the heater. The processor: causes the high-frequency electric power to be output to the bipolar electrodes and detects a parameter that varies depending on tissue volume of the treatment target and that is related to at least one of impedance of the treatment target and the output to the bipolar electrodes; sets a target value related to an output control process for controlling the output to the heater, based on the detected parameter, and controls the output to the heater to modify the treatment target with the heat of the heater, based on the set target value; and then, the smaller the tissue volume of the treatment target, the processor increases the output to the heater and increases a temperature of the heater until at least a predetermined point of time after starting the output control process for controlling the output to the heater, based on the set target value.

First Embodiment

A first embodiment of the disclosed technology will be described below with reference to FIGS. 1 through 9.

Figure 1:
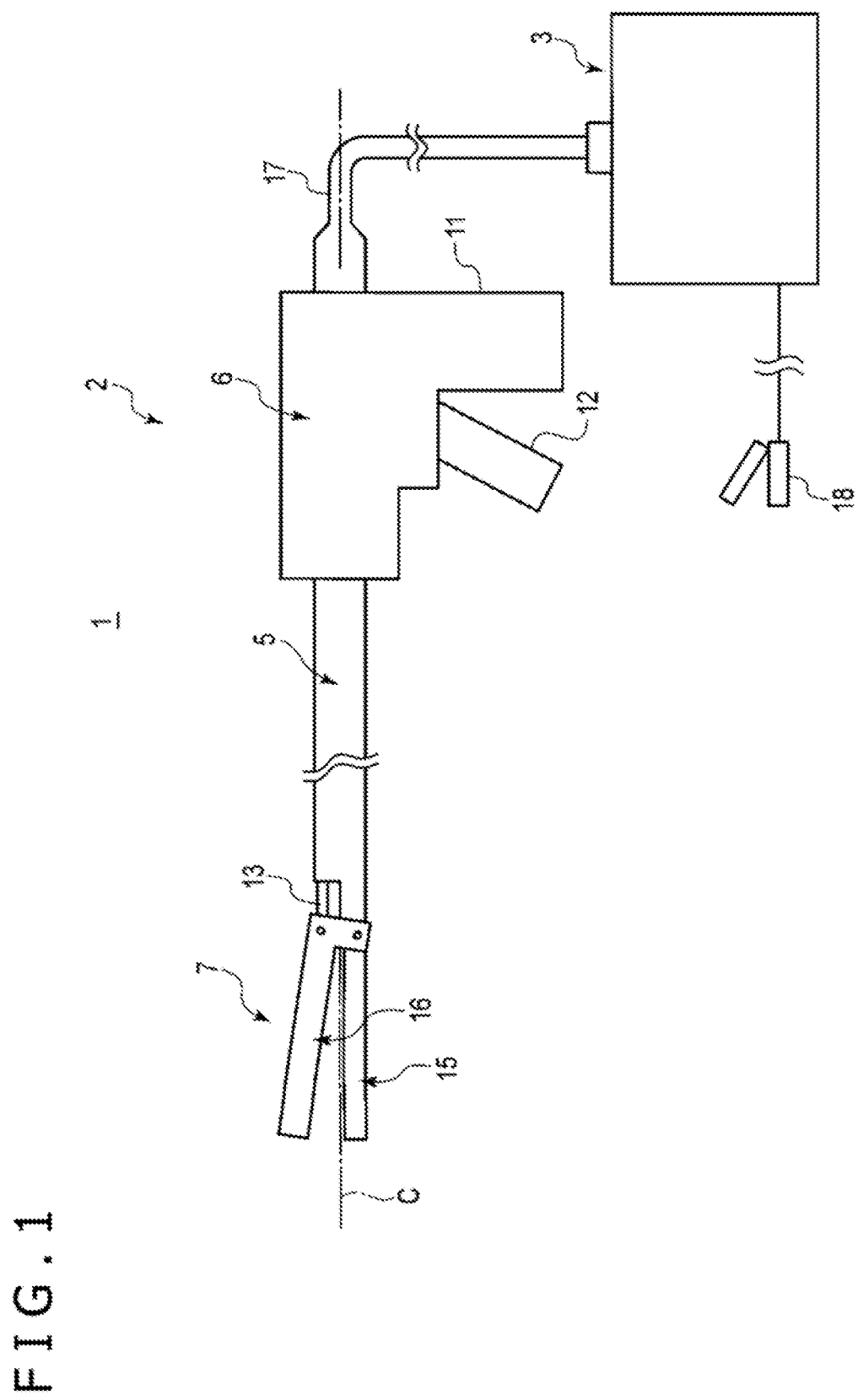
FIG. 1 is a schematic view illustrating a treatment system according to a first embodiment.

FIG. 1 is a view illustrating a treatment system 1 according to the present embodiment. As illustrated in FIG. 1, the treatment system 1 includes a treatment tool 2 and an energy source apparatus 3 for supplying the treatment tool 2 with electric energy. When the treatment tool 2 is in use, the energy source apparatus 3 is used together with the treatment tool 2. The treatment tool 2 includes a shaft 5 having a longitudinal axis C as its central axis. A housing 6 that can be held is coupled to an end, i.e., proximal end, of the shaft 5 in a direction along the longitudinal axis C. An end effector 7 is disposed on the end of the shaft 5 that is opposite to the end where the housing 6 is positioned, i.e., on a distal end of the shaft 5. The housing 6 includes a grip 11 and a handle 12 mounted angularly movably thereon. When the handle 12 is angularly moved with respect to the housing 6, the handle 12 is opened or closed with respect to the grip 11.

The end effector 7 includes a pair of grippers 15 and 16. In the treatment tool 2, a movable member 13 extends along the longitudinal axis C inside or outside of the shaft 5. The movable member 13 has an end, i.e., distal end, connected to the end effector 7. The other end, i.e., proximal end, of the movable member 13 is coupled to the handle 12 in the housing 6. When the handle 12 is opened or closed with respect to the grip 11, the movable member 13 moves along the longitudinal axis C of the shaft 5, opening or closing the grippers 15 and 16. The grippers 15 and 16 are thus capable of gripping a biotissue such as a blood vessel or the like as a treatment target therebetween. According to an embodiment, one of the grippers 15 and 16 is integral with or fixed to the shaft 5, whereas the other of the grippers 15 and 16 is angularly movably mounted on a distal end of the shaft 5. According to another embodiment, both the grippers 15 and 16 are angularly movably mounted on the distal end of the shaft 5. According to an embodiment, an operating member, not illustrated, such as a rotary knob or the like, is mounted on the housing 6. When the operating member is rotated with respect to the housing 6, the shaft 5 and the end effector 7 are rotated about the longitudinal axis C with respect to the housing 6.

A cable 17 has an end connected to the housing 6. The other end of the cable 17 is separably connected to the energy source apparatus 3. The treatment system 1 includes a foot switch 18 as an operating member separate from the treatment tool 2. The foot switch 18 is electrically connected to the energy source apparatus 3. The foot switch 18 inputs an operation for causing the energy source apparatus 3 to output electric energy to the treatment tool 2. According to an embodiment, an operating button or the like that is mounted as an operating member on the housing 6 is included instead of or in addition to the foot switch 18. The energy source apparatus 3 outputs electric energy to the treatment tool 2 in response to an operation entered through the operating member.

Figure 2:
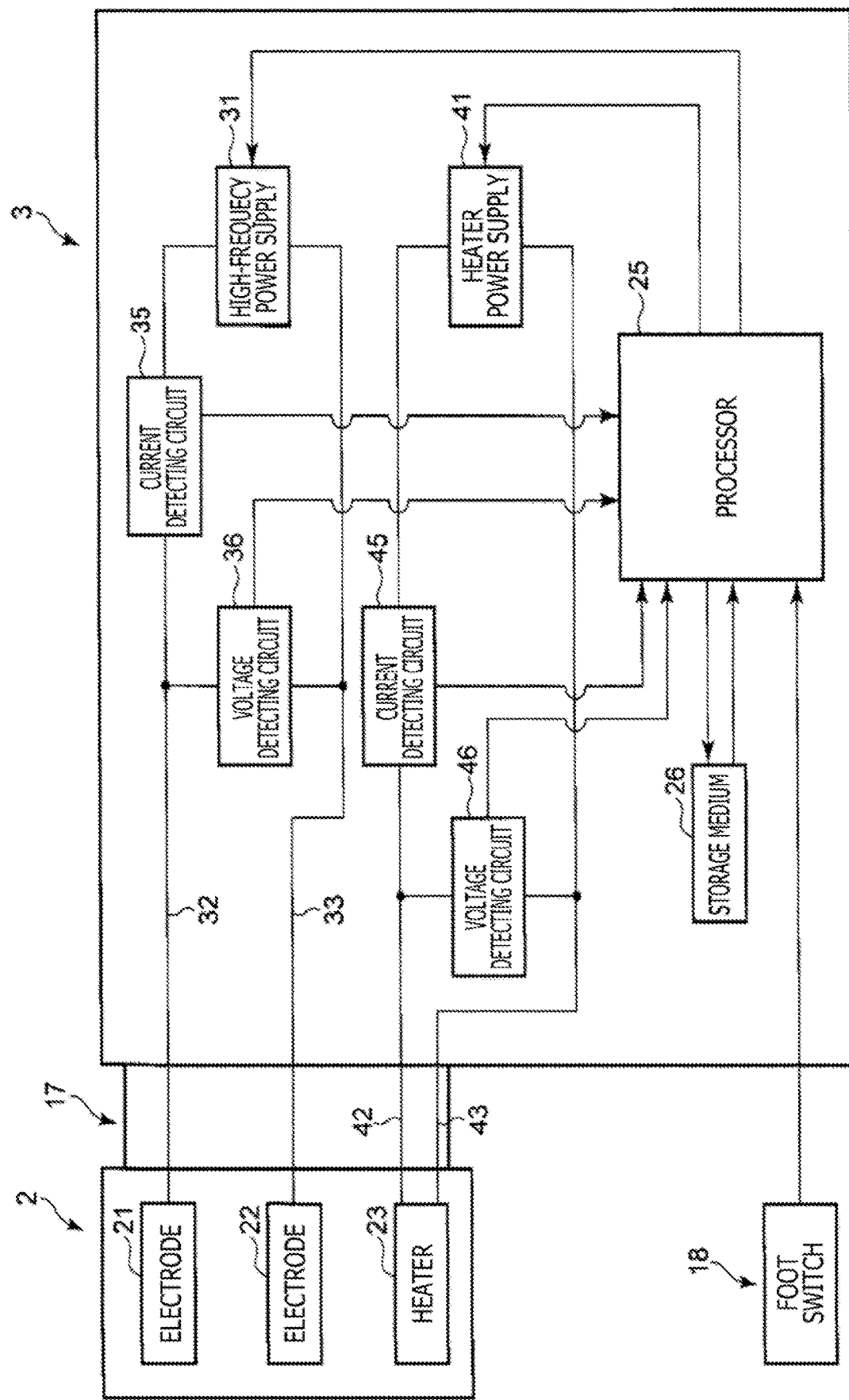
FIG. 2 is a block diagram schematically illustrating an arrangement for supplying electric energy from an energy source apparatus according to the first embodiment to a treatment tool.

FIG. 2 is a diagram illustrating an arrangement for supplying electric energy, i.e., high-frequency electric power P and heater electric power P' to be described hereinafter according to the present embodiment, from the energy source apparatus 3 to the treatment tool 2. As illustrated in FIG. 2, the treatment tool 2 includes an electrode 21 on the gripper 15 and an electrode 22 on the gripper 16. The electrodes 21 and 22 are bipolar electrodes included in the end effector 7. The end effector 7 includes a heater 23 as a heat generating element disposed on at least one of the grippers 15 and 16.

The energy source apparatus 3 includes a processor, i.e., controller, 25 and a storage medium 26. The processor 25 is in the form of an integrated circuit or the like including a central processing unit (CPU), an application specific integrated circuit (ASIC), a field programmable gate array (FPGA), or the like. The energy source apparatus 3 may include only one processor 25 or a plurality of processors 25. The processor 25 carries out a processing sequence according to programs stored in the processor 25 or the storage medium 26. The storage medium 26 stores processing programs used by the processor 25, parameters, functions, and tables used in operations performed by the processor 25, and so on. The processor 25 detects whether or not an operation is entered through the operating member such as the foot switch 18 or the like.

The energy source apparatus 3 includes a high-frequency power supply 31 as an energy output source. The high-frequency power supply 31 includes a waveform generator, a converting circuit, a transformer, and so on. The high-frequency power supply 31 converts electric power from a battery power supply, an outlet power supply, or the like into high-frequency electric power P. The high-frequency power supply 31 is electrically connected to the electrode 21 on the gripper 15 through an electric supply path 32. The high-frequency power supply 31 is also electrically connected to the electrode 22 on the gripper 16 through an electric supply path 33. Each of the electric supply paths 32 and 33 extends in the cable 17, the housing 6, and the shaft 5. Each of the electric supply paths 32 and 33 is in the form of an electric wire or the like. The high-frequency power supply 31 is capable of outputting the converted high-frequency electric power P. While the treatment target is being gripped between the grippers 15 and 16, the high-frequency electric power P output from the high-frequency power supply 31 is supplied through the electric supply paths 32 and 33 to the electrodes 21 and 22. Therefore, a high-frequency current flows through the treatment target between the electrodes, i.e., bipolar electrodes 21 and 22. At this time, the electrodes 21 and 22 have respective potentials that are different from each other. When a high-frequency current having a certain magnitude is applied as treatment energy to the treatment target, the treatment target is modified, sealed and coagulated by the heat caused by the high-frequency current. When an operation is entered through the foot switch 18 or the like, the processor 25 controls the output from the high-frequency power supply 31 to the electrodes 21 and 22 in a manner to be described hereinafter.

The electric paths through which the high-frequency electric power P is output from the high-frequency power supply 31 to the electrodes 21 and 22 include a current detecting circuit 35 and a voltage detecting circuit 36. While the high-frequency electric power P is being output from the high-frequency power supply 31, the current detecting circuit 35 detects the current value of an output current I from the high-frequency power supply 31. At the same time, the voltage detecting circuit 36 detects the voltage value of an output voltage V from the high-frequency power supply 31. An analog signal representing the current value detected by the current detecting circuit 35 and an analog signal representing the voltage value detected by the voltage detecting circuit 36 are converted into digital signals by analog-digital (A/D) converters, not illustrated, or the like. The converted digital signals are transmitted to the processor 25. The processor 25 now acquires information regarding the output current I and the output voltage V from the high-frequency power supply 31. Based on the output current I and the output voltage V that have been acquired, the processor 25 detects impedances of the electric paths through which the high-frequency electric power P is output from the high-frequency power supply 31 to the electrodes 21 and 22. Based on the impedances of the electric paths for the high-frequency electric power P, the processor 25 detects an impedance Z of the gripped treatment target, i.e., a tissue impedance. Based on the output current I and the output voltage V that have been acquired, the processor 25 also detects an electric power value of the high-frequency electric power P, i.e., an electric power value of the output electric power from the high-frequency power supply 31 to the electrodes 21 and 22. The processor 25 controls the output from the high-frequency power supply 31 and a heater power supply 41 using the output current I and the output voltage V that have been acquired, and the impedance Z and the high-frequency electric power P that have been detected, in a manner to be described hereinafter.

The energy source apparatus 3 includes a heater power supply 41 as an energy output source. The heater power supply 41 includes a converting circuit, a transformer, and so on. The heater power supply 41 converts electric power from a battery power supply, an outlet power supply, or the like into heater electric power P'. The heater power supply 41 is electrically connected to the heater 23 through electric supply paths 42 and 43. Each of the electric supply paths 42 and 43 extends in the cable 17, the housing 6, and the shaft 5. Each of the electric supply paths 42 and 43 is in the form of an electric wire or the like. The heater power supply 41 is capable of outputting the converted heater electric power P'. The heater electric power P' that is output is direct current (DC) electric power or alternate current (AC) electric power. When the heater electric power P' output from the heater power supply 41 is supplied through the electric supply paths 42 and 43 to the heater 23, the heater 23 generates heat. While the treatment target is being gripped between the grippers 15 and 16, the heat generated by the heater 23 is applied to the treatment target. When a certain amount of heater heat is applied as treatment energy to the treatment target, the treatment target is modified, sealed and coagulated. When a large amount of heater heat is applied to the treatment target, the treatment target is incised. When an operation is entered through the foot switch 18 or the like, the processor 25 controls the output from the heater power supply 41 to the heater 23 in a manner to be described hereinafter.

The electric paths through which the heater electric power P' is output from the heater power supply 41 to the heater 23 include a current detecting circuit 45 and a voltage detecting circuit 46. While the heater electric power P' is being output from the heater power supply 41, the current detecting circuit 45 detects the current value of an output current I' from the heater power supply 41. At the same time, the voltage detecting circuit 46 detects the voltage value of an output voltage V' from the heater power supply 41. An analog signal representing the current value detected by the current detecting circuit 45 and an analog signal representing the voltage value detected by the voltage detecting circuit 46 are converted into digital signals by A/D converters, not illustrated, or the like. The converted digital signals are transmitted to the processor 25. The processor 25 now acquires information regarding the output current I' and the output voltage V' from the heater power supply 41. Based on the output current I' and the output voltage V' that have been acquired, the processor 25 detects impedances of the electric paths through which the heater electric power P' is output from the heater power supply 41 to the heater 23. Based on the impedances of the electric paths for the heater electric power P', the processor 25 detects a resistance R of the heater 23. The resistance R of the heater 23 varies depending on a temperature T of the heater 23. The storage medium 26 or the like stores a function, a table, or the like that represents the relationship between the temperature T and the resistance R of the heater 23. Based on the detected resistance R and the stored relationship between the temperature T and the resistance R, the processor 25 detects the temperature T of the heater 23. Based on the output current I' and the output voltage V' that have been acquired, the processor 25 also detects an electric power value of the heater electric power P', i.e., an electric power value of the output electric power from the heater power supply 41 to the heater 23. The processor 25 controls the output from the heater power supply 41 using the output current I' and the output voltage V' that have been acquired and the temperature T, i.e., the resistance R, and the heater electric power P' that have been detected, in a manner to be described hereinafter.

Next, operation and advantages of the energy source apparatus 3 and the treatment system 1 will be described below. For performing a treatment using the treatment system 1, the treatment tool 2 is connected through the cable 17 to the energy source apparatus 3. The surgeon holds the housing 6 and inserts the end effector 7 into a body cavity such as an abdominal cavity or the like. While a treatment target such as a biotissue or the like is being positioned between the grippers 15 and 16, the surgeon closes the handle 12 on the grip 11. The grippers 15 and 16 are now closed, gripping the treatment target therebetween. When the surgeon enters an operation through the operating member such as the foot switch 18 or the like while the treatment target is being gripped, the output from the high-frequency power supply 31 to the electrodes 21 and 22 and the output from the heater power supply 41 to the heater 23 are controlled. When the high-frequency electric power P is supplied to the electrodes 21 and 22, a high-frequency current flows through the treatment target as described hereinbefore. When the heater electric power P' is supplied to the heater 23, heat generated by the heater 23 is applied to the treatment target. The treatment target is treating using the high-frequency current and the heater heat as treatment energy. In this embodiment, the treatment target is sealed and coagulated by the high-frequency current and the heater heat.

Figure 3:
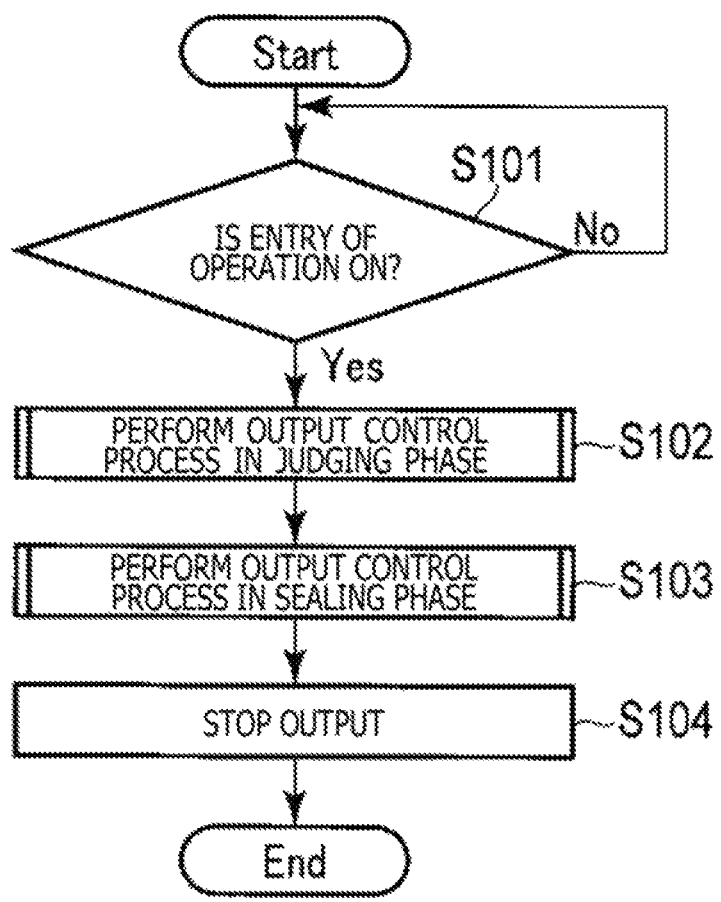
FIG. 3 is a flowchart of a processing sequence carried out by a processor of the energy source apparatus according to the first embodiment.

FIG. 3 is a flowchart of a processing sequence carried out by the processor 25 of the energy source apparatus 3. As illustrated in FIG. 3, the processor 25 determines whether an operation is entered through the operating member such as the foot switch 18 or the like or not, i.e., whether the entry of an operation is ON or OFF (S101). If an operation is not entered (S101—No), then processing returns to S101. In other words, the processor 25 waits until an operation is entered through the operating member. If an operation is entered through the operating member (S101—Yes), then the processor 25 performs an output control process in a judging phase on the output from the high-frequency power supply 31 and the output from the heater power supply 41 (S102).

When the output control process in the judging phase is finished, the processor 25 performs an output control process in a sealing phase, i.e., a coagulating phase, on the output from the high-frequency power supply 31 and the output from the heater power supply 41 (S103). When the output control process in the sealing phase is finished, the processor 25 causes the high-frequency power supply 31 and the heater power supply 41 to stop the outputs (S104).

Figure 4:
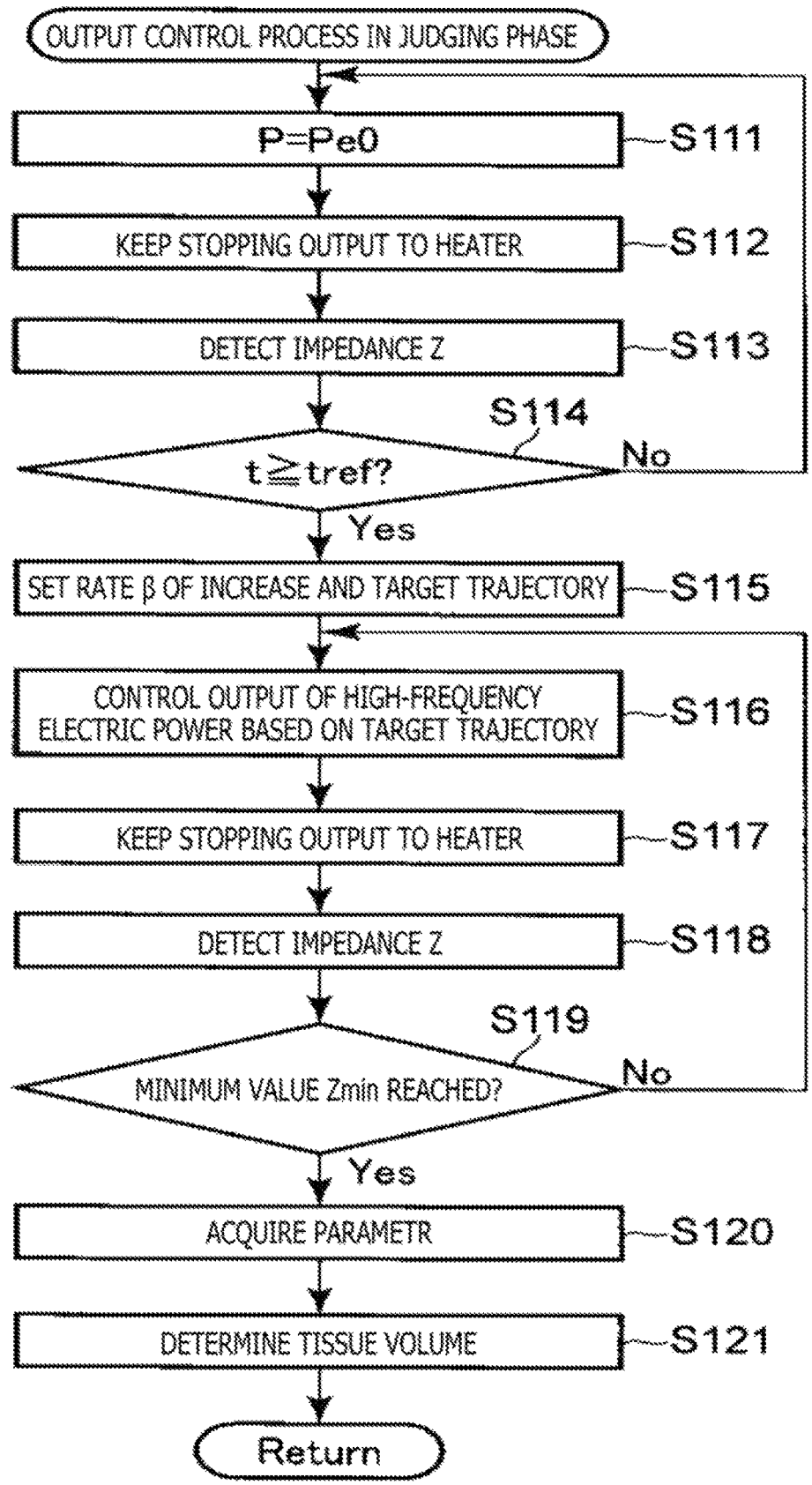
FIG. 4 is a flowchart of a processing sequence carried out by the processor according to the first embodiment in an output control process in a judging phase.

FIG. 4 is a flowchart of a processing sequence carried out by the processor 25 in the output control process in the judging phase (S102). In the judging phase, the processor 25 causes the high-frequency power supply 31 to start to output the high-frequency electric power P to the electrodes 21 and 22. According to the present embodiment, when the high-frequency electric power P starts to be output, the processor 25 causes the high-frequency power supply 31 to output the high-frequency electric power P at a chronologically constant electric power value Pe (S111). At this time, the output current I and the output voltage V from the high-frequency power supply 31 are adjusted to keep the output electric power from the high-frequency power supply 31 as the constant electric power value Pe. According to the present embodiment, the electric power value Pe is a fixed value Pe0. Further, even when the output from the high-frequency power supply 31 is started, the processor 25 keeps stopping the output from the heater power supply 41 to the heater 23 (S112).

Then, the processor 25 detects the impedance Z based on the output current I and the output voltage V from the high-frequency power supply 31 (S113). Then, the processor 25 determines whether or not a time t from the start, used as a reference, of the output from the high-frequency power supply 31 is equal to or larger than a reference time tref (S114). In other words, it is determined whether the reference time tref has elapsed from the start of the output from the high-frequency power supply 31 or not. If the time t is smaller than the reference time tref (S114—No), then processing goes back to step S111, and the steps from S111 are successively carried out. Note that the judging phase is divided into a first phase until the reference time tref elapses and a second phase after the point of time when the reference time tref has elapsed. If the time t is equal to or larger than the reference time tref (S114—Yes), then the processor 25 switches from the output control process in the first phase to the output control process in the second phase, and successively performs the steps from S115 in the second phase.

In the first phase, the processor 25 detects an initial value Ze of the impedance Z as a value representing the impedance Z at the same time as or immediately after the start of the output from the high-frequency power supply 31, based on the impedance Z detected in step S113. The initial value Ze may represent the impedance Z at any point of time in the first phase, or may be an average value, a median value, or the like of the impedance Z in the first phase. The reference time tref is of a fixed value, for example, and is a short time of approximately 100 ms. Therefore, the time during which the output control process in the first phase is carried out is short and instantaneous. Consequently, the output control process in the first phase switches to the output control process in the second phase before the impedance Z decreases from the initial value Ze to a minimum value Zmin to be described hereinafter.

In the second phase of the judging phase, the processor 25 sets a rate β of chronological increase of the output voltage V as a target value related to an output control process for controlling the output from the high-frequency power supply 31, based on the initial value Ze detected in the first phase (S115). At this time, the smaller the initial value Ze, the processor 25 sets the rate β of increase of the output voltage V to a larger value. Then, the processor 25 sets a target trajectory for the output voltage V in relation to the output control process on the output from the high-frequency power supply 31 in the second phase, based on the set rate β of increase (S115). According to the target trajectory, the output voltage V increases chronologically constantly at the set rate β of increase. Therefore, the smaller the initial value Ze, the processor 25 sets the gradient of the target trajectory to a larger value, and sets the value on the target trajectory to a larger value at each point of time in the second phase. Then, the processor 25 controls the output from the high-frequency power supply 31 to the electrodes 21 and 22 in a manner to have the output voltage V vary along the target trajectory (S116). In the second phase, since the output from the high-frequency power supply 31 is controlled as described hereinabove, the treatment target is modified by the high-frequency current applied thereto. In the second phase, the processor 25 stills keeps stopping the output from the heater power supply 41 to the heater 23 (S117).

Then, the processor 25 detects the impedance Z of the treatment target based on the output current I and the output voltage V from the high-frequency power supply 31 (S118). When the second phase starts, the impedance Z decreases chronologically from the initial value Ze. As the water in the treatment target starts to be boiled, the impedance Z starts to increase chronologically. Therefore, at the point of time when the water in the treatment target starts to be boiled or immediately close to that point of time, there occurs a minimum value Zmin of the impedance Z where the impedance Z switches from a chronologically decreasing state to a chronologically increasing state. In the second phase, the processor 25 determines whether the impedance Z has reached the minimum value Zmin or not based on the detected impedance Z (S119). Note that, according to an embodiment, the processor 25 detects the time when the impedance Z switches from the chronologically decreasing state to the chronologically increasing state in determining whether the impedance Z has reached the minimum value Zmin or not. Then, the processor 25 determines that the impedance Z has reached the minimum value Zmin at the time of switching based on the fact that the impedance Z has increased a reference value or more from the time of switching or that the impedance Z has been continuously larger than at the time of switching during a referent time or more from the time of switching.

If the processor 25 determines that the impedance Z has not reached the minimum value Zmin (S119—No), then processing goes back to step S116, and the steps from S116 are successively carried out. In the second phase, therefore, the processor 25 causes the output to the electrodes 21 and 22 to be continued until the processor 25 detects that the impedance Z has reached the minimum value Zmin. If the processor 25 determines that the impedance Z has reached the minimum value Zmin (S119—Yes), then the processor 25 detects and acquires a parameter in the judging phase that is related to the impedance Z based on the impedance Z or the like detected in steps S113 and S118 (S120). At this time, the processor 25 detects, as the parameter hereinabove, at least one of the initial value Ze of the impedance, the minimum value Zmin, a rate α of reduction of the impedance Z down to the minimum value Zmin, and a duration time Ya of the second phase, for example. Here, the duration time Ya is a time from the start of the second phase to the time when it is detected that the impedance Z has reached the minimum value Zmin. Therefore, the time when the processor 25 detects the minimum value Zmin of the impedance Z is the time when the second phase is ended, i.e., the time when the judging phase is ended and the sealing phase is started. Note that the time when the minimum value Zmin is detected is subsequent to a point of time when the impedance Z has reached the minimum value Zmin, e.g., immediately after the point of time when the impedance Z has reached the minimum value Zmin.

In the second phase, the processor 25 determines tissue volume of the treatment target as a state of the treatment target based on the detected parameter hereinabove, i.e., Ze, Zmin, α, Ya, or the like, (S121). The parameter hereinabove, i.e., Ze, Zmin, α, Ya, or the like, varies depending on the tissue volume of the treatment target, such as the thickness of a blood vessel as the treatment target, for example. According to an embodiment, the smaller the initial value Ze, the processor 25 determines that the tissue volume is larger. The longer the duration time Ya, the processor 25 determines that the tissue volume is larger. In addition, the smaller the minimum value Zmin, the processor 25 determines that the tissue volume is larger. The larger the rate α of reduction, the processor 25 determines that the tissue volume is larger. When the tissue volume is determined, the processor 25 puts an end to the output control process in the judging phase and starts the output control process in the sealing phase.

Figure 5:
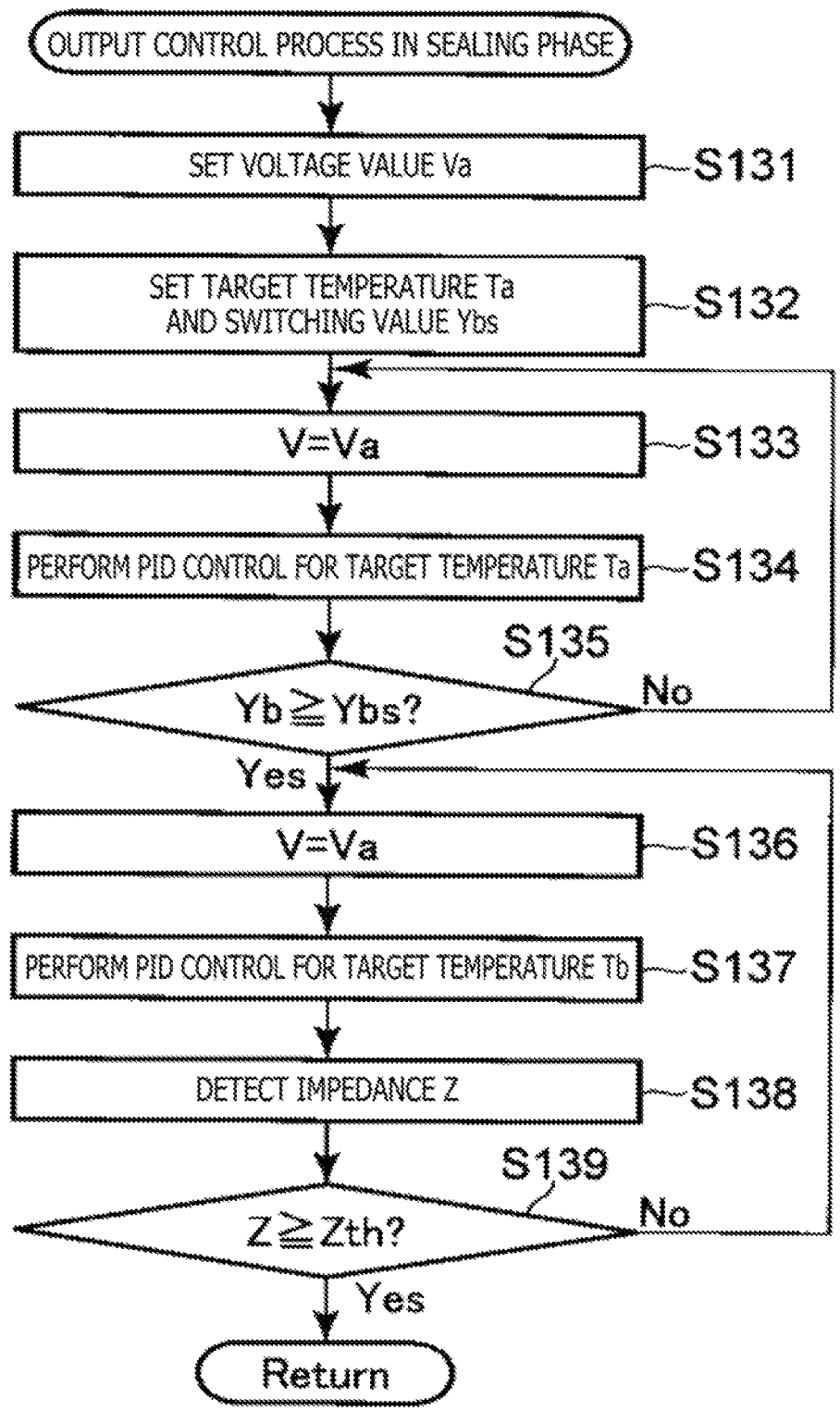
FIG. 5 is a flowchart of a processing sequence carried out by the processor according to the first embodiment in an output control process in a sealing phase.

FIG. 5 is a flowchart of a processing sequence carried out by the processor 25 in the output control process in the sealing phase, i.e., a third phase, (S103). In the sealing phase, the processor 25 sets a voltage value Va of the output voltage V as a target value with respect to the output control process for controlling the output from the high-frequency power supply 31, based on the parameter hereinabove, i.e., Ze, Zmin, α, Ya, or the like, detected in the judging phase, i.e., the determined tissue volume of the treatment target (S131). At this time, the smaller the minimum value Zmin, the processor 25 sets the voltage value Va to a larger value, and the longer the duration time Ya, the processor 25 sets the voltage value Va to a larger value. Therefore, the larger the tissue volume, the larger the voltage value Va is set. Furthermore, the processor 25 sets a target temperature Ta, i.e., a first target temperature, for the heater 23 as a target value related to an output control process for controlling the output from the heater power supply 41, based on the detected parameter hereinabove, i.e., Ze, Zmin, α, Ya, or the like, i.e., the determined tissue volume of the treatment target (S132). In setting the target temperature Ta, there is used a function, a table, or the like that represents the relationship of the parameter hereinabove, i.e., Ze, Zmin, α, Ya, or the like, to target temperatures Ta stored in the storage medium 26, for example. At this time, the larger the minimum value Zmin, for example, the processor 25 sets the target temperature Ta to a higher value, and the shorter the duration time Ya, the processor 25 sets the target temperature Ta to a higher value. Therefore, for example, the thinner a blood vessel as the treatment target, i.e., the smaller the tissue volume, the higher the target temperature Ta, i.e., the first target temperature, is set. Further, the target temperature Ta may be set in a temperature range in which the treatment target is sealed or coagulated by the heater heat. For example, the target temperature Ta is set in a temperature range from 100° C. inclusive to 200° C. inclusive. Therefore, the target temperature Ta that is set is lower than a temperature for incising the treatment target with the heater heat, e.g., a temperature higher than 200° C., i.e., in excess of 200° C.

There is defined a duration time Yb of the output control process for controlling the output to the heater 23 based on the target temperature Ta. The duration time Yb is of the same length as an elapsed time from the start of the sealing phase. When the target temperature Ta is set, the processor 25 sets a switching value Ybs for the duration time Yb based on the detected parameter hereinabove, i.e., Ze, Zmin, α, Ya, or the like, i.e., the determined tissue volume of the treatment target (S132). At this time, the larger the minimum value Zmin, the processor 25 sets the switching value Ybs to a shorter value, and the shorter the duration time Ya, the processor 25 sets the switching value Ybs to a shorter value. Thus, the smaller the tissue volume, the shorter the switching value Ybs is set to. Then, the processor 25 carries out a constant voltage control process for keeping the output voltage V chronologically constant at the set voltage value Va with respect to the output from the high-frequency power supply 31 (S133). At this time, the larger the tissue volume, the higher the voltage value Va and hence the higher the output from the high-frequency power supply 31.

According to the present embodiment, when the sealing phase is started, the processor 25 causes the heater power supply 41 to start the output to the heater 23. At this time, the processor 25 carries out a proportional integral differential (PID) control process for the set target temperature Ta, i.e., the first target temperature, on the output from the heater power supply 41 to the heater 23 (S134). Specifically, an output control process is performed on the output to the heater 23 to cause the temperature T of the heater 23 to reach the target temperature Ta and keep the temperature T at the target temperature Ta. According to the PID control process for the target temperature Ta, the processor 25 detects the resistance R of the heater 23 based on the output current I' and the output voltage V' from the heater power supply 41 and detects the temperature T of the heater 23 based on the detected resistance R, as described hereinbefore. Then, the processor 25 adjusts the output electric power, i.e., the heater electric power P', the output current I', and the output voltage V' to the heater 23, based on the temperature deviation between the target temperature Ta and the temperature T of the heater 23, a time integral value of the temperature deviation, i.e., an integrated value of the temperature deviation, and a time differential value of the temperature deviation, i.e., a time rate of change of the temperature deviation, causing the temperature T to reach the target temperature Ta and maintaining the temperature T at the target temperature Ta. For example, if the temperature deviation between the target temperature Ta and the temperature T is large, then the processor 25 causes the heater power supply 41 to output the heater electric power P' at a large electric power value. If the temperature deviation between the target temperature Ta and the temperature T is small, and the temperature deviation is zero, then the processor 25 causes the heater power supply 41 to output the heater electric power P' at a small electric power value.

Then, the processor 25 determines whether or not the duration time Yb of the output control process for controlling the output to the heater 23 based on the target temperature Ta is equal to or larger than the switching value Ybs (S135). If the duration time Yb is smaller than the switching value Ybs (S135—No), then processing goes back to step S133, and the steps from S133 are successively carried out. In the sealing phase, therefore, until the duration time Yb becomes equal to or larger than the switching value Ybs, the processor 25 continues the output control process for controlling the output to the electrodes 21 and 22 at the voltage value Va and the output control process for controlling the output to the heater 23 based on the target temperature Ta, continuously modifying the treatment target with the high-frequency current and the heater heat applied thereto. Here, there are defined a minimum value Ybsmin for the set switching value Ybs and a predetermined point of time at which the minimum value Ybsmin for the switching value Ybs has elapsed from the start of the output control process for controlling the output to the heater 23 based on the target temperature Ta, i.e., a target value. According to the present embodiment, since the processor 25 performs the processing sequence hereinabove, from the start of the sealing phase to at least the predetermined point of time hereinabove, the smaller the tissue volume based on the parameter hereinabove, i.e., Ze, Zmin, α, Ya, or the like, the higher the output to the heater 23 and the higher the temperature T of the heater 23. If the duration time Yb is equal to or larger than the switching value Ybs (S135—Yes), the processor 25 finishes the output control process on the output to the heater 23 based on the target temperature Ta, i.e., the first target temperature. Therefore, the switching value Ybs for the duration time Yb is used in determining whether to switch from the output control process on the output to the heater 23 based on the target temperature Ta, i.e., whether to finish the output control process on the output to the heater 23 based on the target temperature Ta. Note that, even after the point of time when the processor 25 has determined that the duration time Yb has reached the switching value Ybs, the processor 25 carries out the constant voltage control process on the output from the high-frequency power supply 31 at the voltage value Va hereinabove (S136).

After the point of time when the processor 25 has determined that the duration time Yb has reached the switching value Ybs, the processor 25 carries out a PID control process for a target temperature Tb, i.e., a second target temperature, that is different from the target temperature Ta, i.e., the first target temperature, on the output from the heater power supply 41 (S137). Specifically, the processor 25 switches to an output control process on the output to the heater 23 to cause the temperature T of the heater 23 to reach the target temperature Tb from the target temperature Ta and keep the temperature T at the target temperature Tb. According to the present embodiment, the target temperature Tb is set to a fixed value Tb0 regardless of the tissue volume. The fixed value Tb0 is lower than the set target temperature Ta, i.e., the first target temperature, at any tissue volumes. According to the present embodiment, therefore, based on the fact that the duration time Yb has reached the switching value Ybs, the processor 25 causes the heater power supply 41 to lower the output to lower the temperature of the heater 23 from the target temperature Ta to the target temperature Tb. Note that the fixed value Tb0 of the target temperature Tb is in the temperature range in which the treatment target is sealed or coagulated by the heater heat, and is approximately 100° C., for example.

Then, the processor 25 detects the impedance Z of the treatment target based on the output current I and the output voltage V from the high-frequency power supply 31 (S138). The processor 25 determines whether or not the impedance Z is equal to or larger than a threshold value Zth (S139). According to the present embodiment, the threshold value Zth is a fixed value Zth0. If the impedance Z is smaller than the threshold value Zth (S139—No), then processing goes back to step S136, and the steps from S136 are successively carried out. In the sealing phase, therefore, the processor 25 causes the output to the electrodes 21 and 22 and the output to the heater 23 to be continued, continuously modifying the treatment target with the high-frequency current and the heater heat applied thereto, until the impedance Z becomes equal to or larger than the threshold value Zth. If the impedance Z is equal to or larger than the threshold value Zth (S139—Yes), then the processor 25 puts an end to the output control process in the sealing phase. According to the present embodiment, the processor 25 causes the output to the electrodes 21 and 22 and the output to the heater 23 to be stopped according to the processing of S104. According to the present embodiment, therefore, the threshold value Zth is used in determining whether to finish the sealing phase. In the sealing phase, the water in the treatment target is boiled by the high-frequency current and the heater heat applied thereto. Even after the treatment target has been dehydrated, the temperature of the treatment target increases chronologically due to the high-frequency current and the heater heat applied thereto. In the sealing phase, consequently, the impedance Z increases chronologically.

Figure 6:
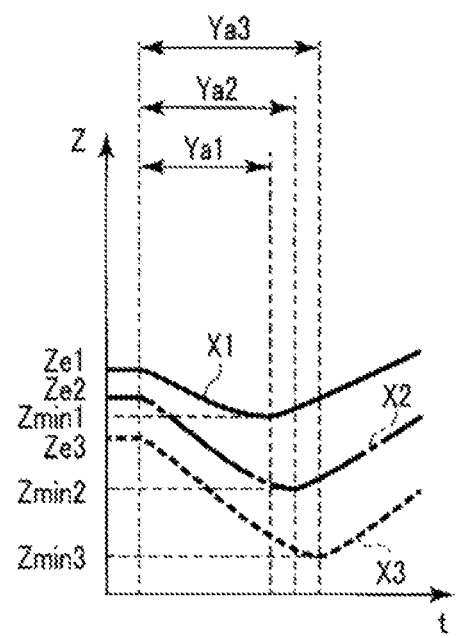
FIG. 6 is a schematic diagram illustrating an example of chronological changes in the impedance of a treatment target in the judging phase in the processing sequence carried out by the processor according to the first embodiment.
Figure 7:
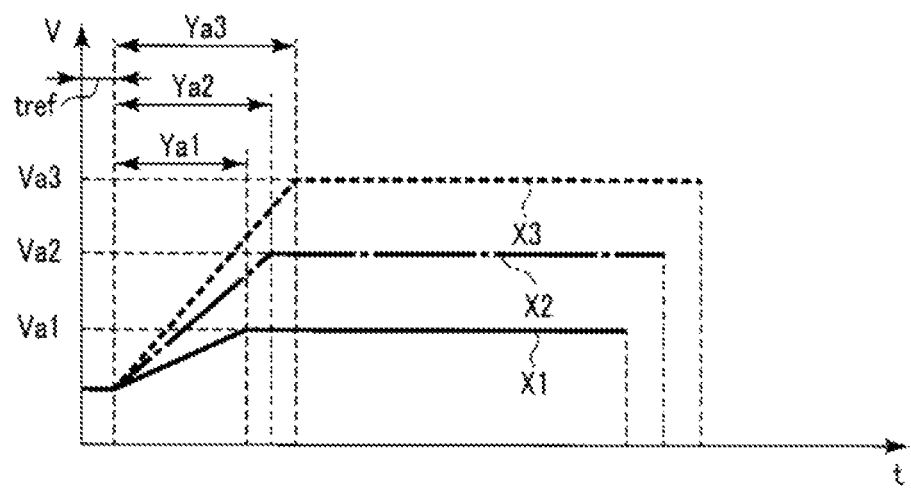
FIG. 7 is a schematic diagram illustrating an example of target trajectories for an output voltage from a high-frequency power supply in case the impedance changes chronologically as illustrated in FIG. 6 in the first embodiment.
Figure 8:
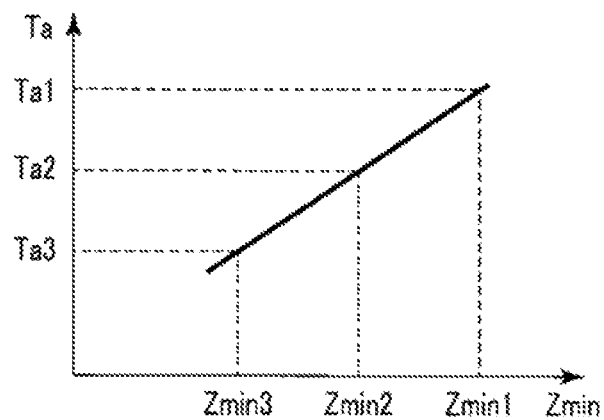
FIG. 8 is a schematic diagram illustrating an example of the relationship between a minimum value of the impedance and a target temperature immediately after the sealing phase has started in the first embodiment.
Figure 9:
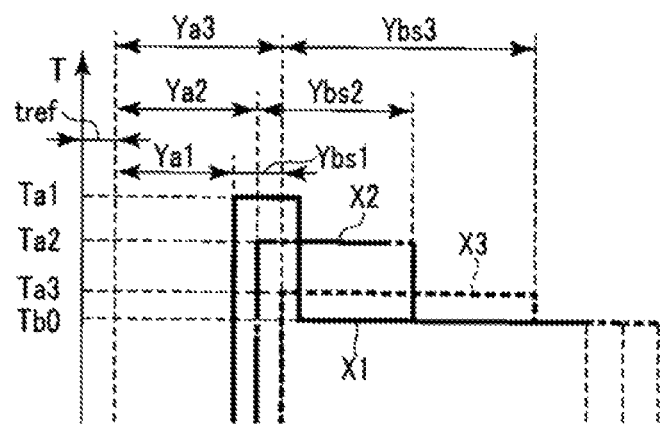
FIG. 9 is a schematic diagram illustrating an example of target trajectories for the temperature of a heater in case the impedance changes chronologically as illustrated in FIG. 6 in the first embodiment.

FIG. 6 is a schematic diagram illustrating an example of chronological changes in the impedance Z of the treatment target in the judging phase in the processing sequence carried out by the processor 25 as described hereinabove. FIG. 7 is a schematic diagram illustrating an example of target trajectories for the output voltage from the high-frequency power supply 31 in case the impedance Z changes chronologically as illustrated in FIG. 6. FIG. 8 is a schematic diagram illustrating an example of the relationship between the minimum value Zmin of the impedance Z and the target temperature Ta immediately after the sealing phase has started. FIG. 9 is a schematic diagram illustrating an example of target trajectories for the temperature T of the heater 23 in case the impedance Z changes chronologically as illustrated in FIG. 6. In each of FIGS. 6, 7, and 9, a horizontal axis represents time t from the start, used as a reference, of the judging phase. In FIG. 6, a vertical axis represents the impedance Z. In FIG. 7, a vertical axis represents the output voltage V from the high-frequency power supply 31. In FIG. 9, a vertical axis represents the temperature T of the heater 23. In FIG. 8, a horizontal axis represents the minimum value Zmin and a vertical axis the set target temperature Ta. Each of FIGS. 6, 7 and 9 illustrates the chronological changes in three states, i.e., tissue states, X1 through X3. The states X1 through X3 indicate tissue volumes of the treatment target that are different from each other. In the state X1, the tissue volume of the treatment target is smaller because the blood vessel as the treatment target is thin, etc. than in the state X2. In the state X3, the tissue volume of the treatment target is larger because the blood vessel as the treatment target is thick, etc. than in the state X2. In each of FIGS. 6, 7 and 9, the chronological changes in the state X1 are indicated by the solid-line curve, the chronological changes in the state X2 by the dot-and-dash-line curve, and the chronological changes in the state X3 by the broken-line curve.

As described hereinabove, the parameter, i.e., Ze, Zmin, α, or Ya, detected in the judging phase and related to the impedance Z varies depending on the state of the treatment target such as the tissue volume of the treatment target or the like. Specifically, the larger the tissue volume, the smaller each of the initial value Ze and the minimum value Zmin. Furthermore, the larger the tissue volume, the larger the rate α of reduction of the impedance Z down to the minimum value Zmin, and the longer the duration time Ya of the second phase. In the examples illustrated in FIGS. 6 through 9, actually, the initial value Ze1 in the state X1 is larger than the initial value Ze2 in the state X2, and the initial value Ze3 in the state X3 is smaller than the initial value Ze2 in the state X2. Further, the minimum value Zmin1 in the state X1 is larger than the minimum value Zmin2 in the state X2, and the minimum value Zmin3 in the state X3 is smaller than the minimum value Zmin2 in the state X2. Furthermore, the rate α1 of reduction of the impedance Z down to the minimum value Zmin1 in the state X1 is smaller than the rate α2 of reduction of the impedance Z down to the minimum value Zmin2 in the state X2, and the rate α3 of reduction of the impedance Z down to the minimum value Zmin3 in the state X3 is larger than the rate α2 of reduction of the impedance Z down to the minimum value Zmin2 in the state X2. In addition, the duration time Ya1 of the second phase in the state X1 is shorter than the duration time Ya2 of the second phase in the state X2, and the duration time Ya3 of the second phase in the state X3 is longer than the duration time Ya2 of the second phase in the state X2.

According to the present embodiment, as described hereinabove, the smaller the initial value Ze of the impedance Z, i.e., the larger the tissue volume, the rate β of increase of the output voltage V in the second phase is set to a larger value, and the gradient of the target trajectory for the output voltage V in the second phase is set to a larger value. In the state X1, actually, the rate β of increase of the output voltage V and the gradient of the target trajectory in the second phase are set to smaller values than in the state X2. In addition, in the state X3, the rate β of increase of the output voltage V and the gradient of the target trajectory in the second phase are set to larger values than in the state X2. Moreover, according to the present embodiment, as described hereinabove, the smaller the minimum value Zmin of the impedance Z and the longer the duration time Ya of the second phase, for example, it is judged that the tissue volume of the treatment target is larger. Therefore, the voltage value Va of the output voltage in the constant voltage control process in the sealing phase is set to a larger value. Actually, the voltage value Va1 in the sealing phase set in the state X1 is smaller than the voltage value Va2 in the sealing phase set in the state X2. In addition, the voltage value Va3 in the sealing phase set in the state X3 is larger than the voltage value Va2 in the sealing phase set in the state X2.

Furthermore, according to the present embodiment, as described hereinabove, the larger the minimum value Zmin of the impedance Z and the shorter the duration time Ya of the second phase, for example, it is judged that the tissue volume of the treatment target is smaller. Therefore, the target temperature Ta, i.e., the first target temperature, for the heater 23 immediately after the sealing phase has started is set to a higher value. For example, providing the target temperature Ta is set based on the minimum value Zmin, the target temperature Ta1 set in the state X1 for the minimum value Zmin1 is higher than the target temperature Ta2 set in the state X2 for the minimum value Zmin2 that is smaller than the minimum value Zmin. In addition, the target temperature Ta3 set in the state X3 for the minimum value Zmin3 is lower than the target temperature Ta2 set in the state X2 for the minimum value Zmin2 that is larger than the minimum value Zmin3. According to the present embodiment, however, regardless of the tissue volume, i.e., in either one of the states X1 through X3, when the duration time Yb of the output control process based on the target temperature Ta reaches the switching value Ybs, the output control process for controlling the output to the heater 23 based on the target temperature Ta is finished. Then, the output control process for controlling the output to the heater 23 is carried out to lower the temperature of the heater 23 from the target temperature Ta, i.e., the first target temperature, to the target temperature Tb, i.e., the second target temperature, and maintain the heater 23 at the target temperature Tb.

Furthermore, according to the present embodiment, as described hereinabove, the larger the minimum value Zmin of the impedance Z and the shorter the duration time Ya of the second phase, for example, it is judged that the tissue volume of the treatment target is smaller. Therefore, the switching value Ybs for the duration time Yb is set to a shorter value. Consequently, the smaller the tissue volume of the treatment target, the shorter the time during which the output control process for controlling the output to the heater 23 based on the target temperature Ta is carried out. Actually, the switching value Ybs1 set in the state X1 is shorter than the switching value Ybs2 set in the state X2. The time during which the output control process for controlling the output to the heater 23 based on the target temperature Ta1 in the state X1 is carried out is shorter than the time during which the output control process for controlling the output to the heater 23 based on the target temperature Ta2 in the state X2 is carried out. The switching value Ybs3 set in the state X3 is longer than the switching value Ybs2 set in the state X2. The time during which the output control process for controlling the output to the heater 23 based on the target temperature Ta3 in the state X3 is carried out is longer than the time during which the output control process for controlling the output to the heater 23 based on the target temperature Ta2 in the state X2 is carried out.

Because the foregoing processing is carried out, in treating a treatment target whose tissue volume is small in the state X1 or the like, the temperature T of the heater 23 is high and the amount of heater heat applied to the treatment target is large immediately after the sealing phase has been started. Therefore, in treating a treatment target whose tissue volume is small, when the sealing phase is started, the treatment target is quickly modified and dehydrated by the heater heat, and quickly modified into a state in which the treatment target is dried to a certain extent. Since the treatment target is quickly modified into a state in which the treatment target is dried to a certain extent, in case the tissue volume of the treatment target is small, the high-frequency current is less likely in the sealing phase to flow into a region of the biotissue other than the treatment target, which is gripped, such as a region positioned outside of the grippers in the widthwise directions thereof with respect to the treatment target. Inasmuch as the high-frequency current is less likely to flow into a region of the biotissue, which is gripped, other than the treatment target, in case the tissue volume of a treatment target is small, the heat caused by the high-frequency current is effectively prevented from spreading outwardly in the widthwise directions of the grippers from the gripped treatment target in the biotissue. In other words, a lateral thermal spread of the heat caused by the high-frequency current is effectively prevented in the biotissue that includes the treatment target. At this time, the high-frequency current flowing in the treatment target is also reduced. However, since the tissue volume is small, the treatment target can appropriately be sealed or coagulated by the reduced high-frequency current.

According to the present embodiment, furthermore, based on the fact that the duration time Yb of the output control process for controlling the output to the heater 23 based on the target temperature Ta becomes equal to or larger than the switching value Ybs, the processor 25 switches to the output control process for lowering the temperature T of the heater 23 to the target temperature Tb. In treating a treatment target whose tissue volume is small, therefore, the temperature T of the heater 23 is increased. After the treatment target has been quickly modified into a state in which it is dried to a certain extent, as described hereinabove, the temperature T of the heater 23 is lowered to a temperature that is suitable for sealing and coagulating the treatment target. Consequently, in treating a treatment target whose tissue volume is small, even if the treatment target is quickly modified into a state in which it is dried to a certain extent, the treatment target is appropriately sealed or coagulated by the heater heat.

According to the present embodiment, furthermore, the smaller the tissue volume, the switching value Ybs for the duration time Yb is set to a shorter value. Therefore, in treating a treatment target whose tissue volume is small, the time during which the temperature T of the heater 23 is high, i.e., the time during which the treatment target is quickly modified and dehydrated by the heater heat, is short. Consequently, even if the tissue volume of a treatment target is small, the time during which the temperature T of the heater 23 becomes a temperature suitable for sealing and coagulating the treatment target, i.e., the time during which the output control process based on the target temperature Tb is carried out, is increased to increase the sealability and coagulatability of the treatment target. Further, as the time during which the temperature T of the heater 23 is high is short, even when the tissue volume of a treatment target is small, the heater heat is effectively prevented in the sealing phase from spreading outwardly in the widthwise directions of the grippers from the gripped treatment target in the biotissue. In other words, a lateral thermal spread of the heater heat is effectively prevented in the biotissue that includes the treatment target. In addition, as the time during which the temperature T of the heater 23 is high is short, in case the tissue volume of a treatment target is small, an excessive output to the heater 23 is restrained.

Furthermore, in treating a treatment target whose tissue volume is large in the state X3 or the like, the temperature T of the heater 23 is not high and the amount of heater heat applied to the treatment target is not large immediately after the sealing phase has been started. Therefore, in treating a treatment target whose tissue volume is large, even when the sealing phase is started, the treatment target is not quickly modified and dehydrated by the heater heat, and is gradually modified and dehydrated by the heater heat. Therefore, even when a certain time has elapsed from the start of the sealing phase, the treatment target remains wet to a certain extent. Because of this, even though the tissue volume of the treatment target is large, the high-frequency current flows appropriately into the gripped treatment target in its entirety in the sealing phase, appropriately sealing or coagulating the treatment target. According to the present embodiment, moreover, the larger the tissue volume, the higher the output from the high-frequency power supply 31 in the sealing phase. As a result, the sealability and coagulatability of the treatment target are increased. In addition, with the treatment target being modified and dehydrated by the heater heat, the high-frequency current is restrained from flowing into a region of the biotissue other than the treatment target, i.e., a gripped region of the biotissue. Consequently, in case the tissue volume of a treatment target is large, a high-frequency current required to appropriately seal or coagulate the treatment target is maintained, while at the same time a lateral thermal spread of the heat caused by the high-frequency current is effectively reduced in the biotissue that includes the treatment target.

Modifications

Figure 10:
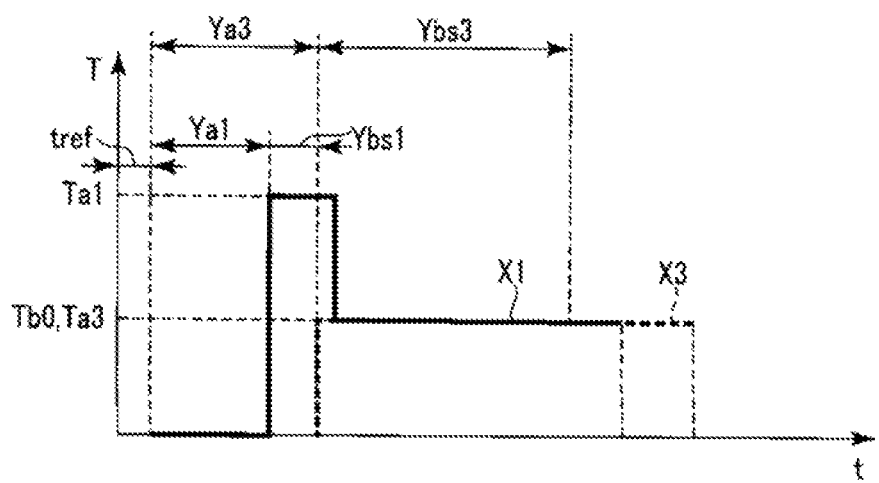
FIG. 10 is a schematic diagram illustrating an example of a target trajectory for the temperature of a heater in case a processor according to a first modification carries out a processing sequence.
Figure 11:
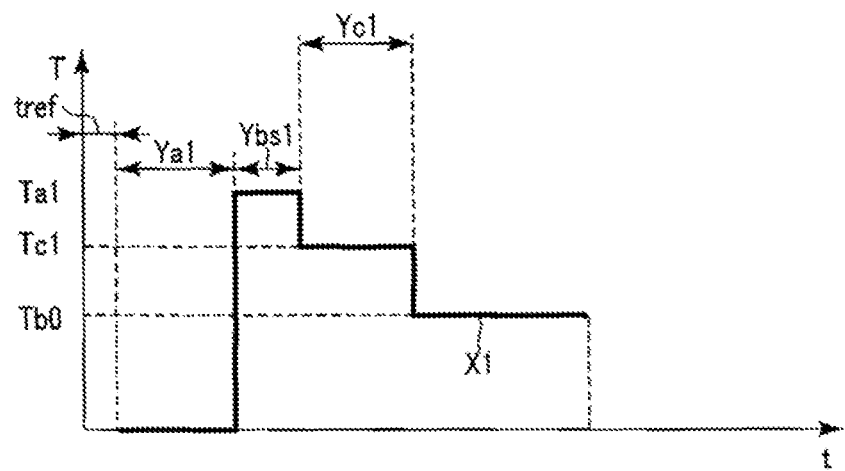
FIG. 11 is a schematic diagram illustrating an example of a target trajectory for the temperature of a heater in case a processor according to a second modification carries out a processing sequence.
Figure 12:
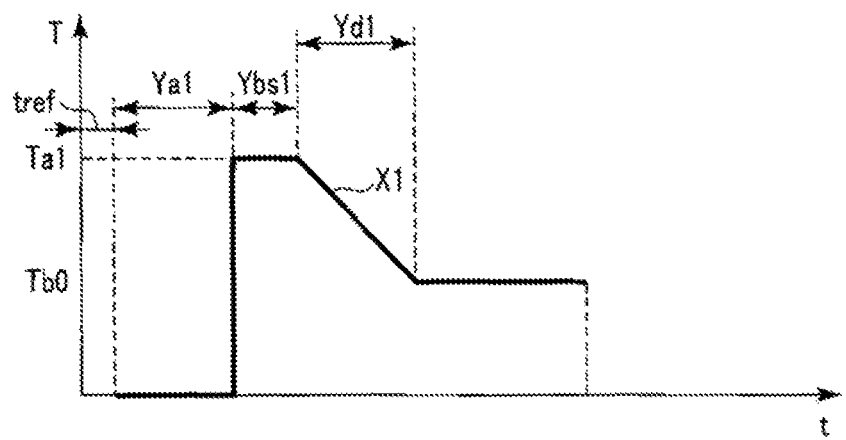
FIG. 12 is a schematic diagram illustrating an example of a target trajectory for the temperature of a heater in case a processor according to a third modification carries out a processing sequence.

First through third modifications will be described hereinafter with reference to FIGS. 10 through 12. FIGS. 10 through 12 illustrate examples of target trajectories for the temperature T of the heater 23. FIG. 10 illustrates an example of the first modification. FIG. 11 illustrates an example of the second modification. FIG. 12 illustrates an example of the third modification. In each of FIGS. 10 through 12, a horizontal axis represents time t from the start of the judging phase used as a reference, and a vertical axis the temperature T of the heater 23. In FIG. 10, the target trajectory in the state X1 hereinabove is indicated by the solid-line curve, and the target trajectory in the state X3 hereinabove by the broken-line curve. In each of FIGS. 11 and 12, the target trajectory in the state X1 is indicated by the solid-line curve.

According to the first modification illustrated in FIG. 10, if the determined tissue volume is equal to or larger than a reference value, then the processor 25 sets the target temperature Ta, i.e., the first target temperature, immediately after the start of the sealing phase to a value identical to the target temperature Tb, i.e., the second target temperature, after the point of time when it is determined that the duration time Yb is equal to or larger than the switching value Ybs. In the state X3, actually, the target temperature Ta3 prior to the point of time when it is determined that the switching value Ybs3 has elapsed is set to a value identical to the target temperature Tb0 subsequent to the point of time when it is determined that the switching value Ybs3 has elapsed. According to the present modification, however, if the tissue volume in the state X1, X2 or the like is smaller than the reference value, then the target temperature Ta is set to a value higher than the target temperature Tb. The smaller the tissue volume, the target temperature Ta is set to a higher value. According to the present modification, therefore, if the tissue volume is smaller than the reference value, then the processor 25 performs the output control process for lowering the temperature T of the heater 23 from the target temperature Ta to the target temperature Tb based on the fact that the duration time Yb is equal to or larger than the switching value Ybs.

According to the present modification, if it is determined that the tissue volume is equal to or larger than the reference value, then the processor 25 may not set the switching value Ybs in step S132 and may not determine the duration time Yb based on the switching value Ybs in step S135. In this case, the processor 25 sets the target temperature Ta to a value identical to the fixed value Tb0 of the target temperature Tb. Then, the processor 25 continues the output control process for controlling the output to the heater 23 based on the target temperature Ta identical to the fixed value Tb0 until the impedance Z becomes equal to or larger than the threshold value Zth. In other words, the PID control process based on the target temperature Ta set to the fixed value Tb0 is continued until the end of the sealing phase.

According to the second modification illustrated in FIG. 11, the processor 25 switches to the output control process for lowering the temperature of the heater 23 from the target temperature Ta to a target temperature Tc based on the fact that the duration time Yb has become equal to or larger than the switching value Ybs. The target temperature Tc is lower than the target temperature Ta, i.e., the first target temperature, and higher than the target temperature Tb, i.e., the second target temperature. In addition, the target temperature Tc may be of a fixed value Tc0 regardless of the tissue volume, or may be set based on the tissue volume. According to the present modification, the processor 25 carries out an output control process for lowering the temperature of the heater 23 to the target temperature Tc and maintaining the heater 23 at the target temperature Tc, during a reference time Yc. The reference time Yc may be of a fixed value Yc0 regardless of the tissue volume, or may be set based on the tissue volume. Then, the processor 25 switches to an output control process for lowering the temperature of the heater 23 from the target temperature Tc to the target temperature Tb based on the fact that the reference time Yc has elapsed from the start of the output control process for controlling the output to the heater 23 based on the target temperature Tc. In the state X1, actually, the processor 25 switches to the output control process for controlling the output to the heater 23 based on the target temperature Tc1 based on the fact that the duration time Yb has become equal to or larger than the switching value Ybs1. Then, after having performed the output control process for controlling the output to the heater 23 based on the target temperature Tc1 during the reference time Yc1, the processor 25 switches to an output control process for controlling the output to the heater 23 based on the target temperature Tb0.

In the present modification, only one target temperature Tc is set in the temperature range between the target temperature Ta and the target temperature Tb. According to a modification, a plurality of target temperatures are set in the temperature range between the target temperature Ta and the target temperature Tb. In this case, as with the second modification, based on the fact that the duration time Yb has become equal to or larger than the switching value Ybs, the processor 25 lowers the temperature T of the heater 23 stepwise from the target temperature Ta to the target temperature Tb based on the target temperatures set in the temperature range between the target temperature Ta and the target temperature Tb.

Further, according to the third modification illustrated in FIG. 12, based on the fact that the duration time Yb has become equal to or larger than the switching value Ybs, the processor 25 performs an output control process for lowering the temperature T of the heater 23 from the target temperature Ta to the target temperature Tb along a target trajectory. According to the present modification, the target trajectory is represented by a linear function. According to the target trajectory, the temperature T decreases chronologically linearly from the target temperature Ta to the target temperature Tb. According to the target trajectory, furthermore, a reference time Yd is required for the temperature T to lower from the target temperature Ta to the target temperature Tb. The reference time Yd may be of a fixed value Yd0 regardless of the tissue volume, or may be set based on the tissue volume. In the state X1, actually, the processor 25 switches to an output control process for reducing the temperature T chronologically along the target trajectory based on the fact that the duration time Yb has become equal to or larger than the switching value Ybs1. According to the target trajectory set in the state X1, a reference time Yd1 is required for the temperature T to lower from the target temperature Ta to the target temperature Tb. Note that, according to a modification, a target trajectory for the temperature T from the target temperature Ta to the target temperature Tb may be represented by a quadratic function, an exponential function, or the like. In this case, according to the target trajectory, the temperature T decreases chronologically nonlinearly from the target temperature Ta to the target temperature Tb.

Furthermore, according to the embodiment, etc. hereinabove, the target temperature Tb, i.e., the second target temperature, is set to the fixed value Tb0. However, the disclosed technology is not limited to such details. According to a modification, the target temperature Tb is set based on the parameter hereinabove, i.e., Zmin, Ya, or the like, i.e., the tissue volume of the treatment target. In this case, the smaller the tissue volume, the target temperature Tb is set to a lower value, for example. In addition, the target temperature Tb is set in a temperature range for sealing or coagulating the treatment target with the heater heat.

According to the embodiment, etc. hereinabove, the target temperature Ta, i.e., the first target temperature, is set as a target value related to the output control process for controlling the output to the heater 23 in the sealing phase. However, the disclosed technology is not limited to such details. According to a modification, the PID control process based on the target temperature Ta is not performed during a period from the start of the sealing phase until the duration time Yb becomes the switching value Ybs. According to the present modification, however, the processor 25 sets a target value relative to the output control process for controlling the output to the heater 23 in the sealing phase, based on the parameter hereinabove, i.e., Zmin, Ya, or the like, which varies depending on the tissue volume, and controls the output to the heater 23 based on the set target value. At this time, for example, the processor 25 sets a rate of chronological change of the temperature T of the heater 23 as a target value relative to the output control process for controlling the output to the heater 23, based on the parameter, i.e., Zmin, Ya, or the like, during the period from the start of the sealing phase until the duration time Yb becomes the switching value Ybs, and sets a target trajectory for the temperature T based on the rate of change of the temperature T. Then, the processor 25 performs the output control process for controlling the output to the heater 23 based on the target value such as the set rate of change of the temperature T and the target trajectory. According to the present modification, therefore, from the start of the sealing phase until at least a predetermined point of time, the smaller the tissue volume based on the parameter hereinabove, i.e., Ze, Zmin, α, Ya, or the like, the higher the output to the heater 23 and the higher the temperature T of the heater 23. Here, the predetermined point of time refers to a point of time when the minimum value Ybsmin for the switching value Ybs has elapsed from the start of the output control process for controlling the output to the heater 23 based on the set target value, for example.

According to the present modification, the processor 25 causes the output to the heater 23 to be lowered to lower the temperature T of the heater 23 based on the fact that the duration time Yb of the output control process for controlling the output to the heater 23 based on the target value, i.e., the duration time of the sealing phase, has become the switching value Ybs. Then, the smaller the tissue volume based on the parameter hereinabove, i.e., Ze, Zmin, α, Ya, or the like, the processor 25 sets the switching value Ybs to a shorter value.

Figure 13:
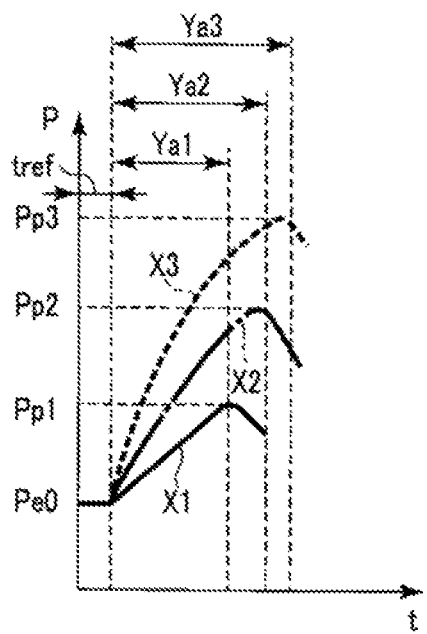
FIG. 13 is a schematic diagram illustrating an example of chronological changes in high-frequency electric power in the judging phase in case a processor according to a fourth modification carries out a processing sequence.
Figure 14:
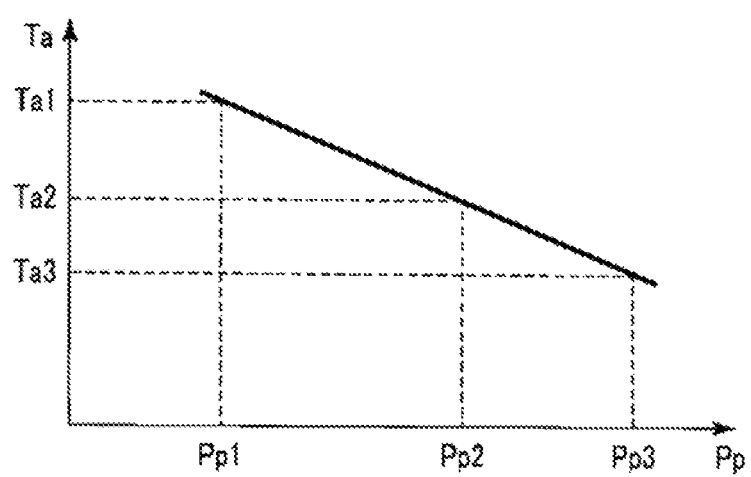
FIG. 14 is a schematic diagram illustrating an example of the relationship between peak electric power of high-frequency electric power and the target temperature immediately after the sealing phase has started in the fourth modification.

According to a modification, moreover, the processor 25 determines the tissue volume of the treatment target based on a parameter relative to either one of the output electric power, i.e., the high-frequency electric power P, the output current I, and the output voltage V from the high-frequency power supply 31 in the judging phase, i.e., a parameter relative to the output from the high-frequency power supply 31 in the judging phase, and sets the target temperature Ta for the heater 23 immediately after the start of the sealing phase. According to a fourth modification illustrated in FIGS. 13 and 14, for example, the processor 25 determines the tissue volume based on the peak electric power Pp of the high-frequency electric power P produced in the second phase of the judging phase, and sets the target temperature Ta. Here, FIG. 13 illustrates an example of chronological changes in the high-frequency electric power P in the judging phase. FIG. 14 illustrates an example of the relationship between the peak electric power Pp of the high-frequency electric power P and the target temperature Ta immediately after the sealing phase has started. In FIG. 13, a horizontal axis represents time t from the start of the judging phase used as a reference, and a vertical axis the high-frequency electric power P. Then, In FIG. 13, the chronological changes in the state X1 hereinabove are indicated by the solid-line curve, and the chronological changes in the state X2 hereinabove by the dot-and-dash-line curve, and the chronological changes in the state X3 hereinabove by the broken-line curve. In FIG. 14, a horizontal axis represents the peak electric power Pp and a vertical axis the target temperature Ta.

If the output control process for controlling the output from the high-frequency power supply 31 is carried out in the same manner as with the first embodiment, for example, in the judging phase, then when the second phase is started after the output of the high-frequency electric power P has been continued at the electric power value Pe0 in the first phase, the high-frequency electric power P increases chronologically. At the point of time when the impedance Z becomes the minimum value Zmin or immediately close to that point of time, the high-frequency electric power P becomes the peak electric power Pp. After having become the peak electric power Pp, the high-frequency electric power P decreases chronologically. The smaller the tissue volume of the treatment target, the smaller the peak electric power Pp. Actually, the peak electric power Pp1 in the state X1 is smaller than the peak electric power Pp2 in the state X2. The peak electric power Pp3 in the state X3 is larger than the peak electric power Pp2 in the state X2. Further, according to the present modification, since the smaller the peak electric power Pp, it is determined that the tissue volume is smaller, the target temperature Ta, i.e., the first target temperature, for the heater 23 immediately after the start of the sealing phase is set to a higher value. For example, the target temperature Ta1 set in the state X1 for the peak electric power Pp1 is higher than the target temperature Ta2 set in the state X2 for the peak electric power Pp2. The target temperature Ta3 set in the state X3 for the peak electric power Pp3 is lower than the target temperature Ta2 set in the state X2 for the peak electric power Pp2 that is smaller than the peak electric power Pp3.

Furthermore, according to the embodiment, etc. hereinabove, the output to the heater 23 is suspended in the judging phase. According to a modification, heater electric power P' is output to the heater 23 in the judging phase. However, in the judging phase, the processor 25 causes the heater power supply 41 to lower the output to lower the temperature T of the heater 23 to such an extent that the treatment target will not be modified by the heater heat.

According to a modification, furthermore, the rate β of increase of the output voltage V that is a target value related to the output control process for controlling the output from the high-frequency power supply 31 in the second phase is of a fixed value β0 regardless of the initial value Ze, i.e., regardless of the tissue volume of the treatment target. In this case, the processor 25 does not perform the processing of S115 for setting the rate β of increase and the target trajectory based on the initial value Ze. According to a modification, moreover, the voltage value Va that is a target value related to the output control process for controlling the output from the high-frequency power supply 31 in the sealing phase is of a fixed value Va0 regardless of the parameters described hereinbefore, i.e., Ze, Ya, Zmin, α, Pp, etc., i.e., regardless of the tissue volume of the treatment target. In this case, the processor 25 does not perform the processing of S131 for setting the voltage value Va based on the parameters, i.e., Ze, Ya, Zmin, α, Pp, etc. According to a modification, furthermore, either one of a constant power control process for keeping the output electric power from the high-frequency power supply 31, i.e., the high-frequency electric power P, at a constant electric power value Pa, and a constant current control process for keeping the output current I therefrom at a constant current value Ia is carried out in the sealing phase. For performing the constant power control process, the processor 25 may set the electric power value Pa that is a target value to a fixed value Pa0 regardless of the tissue volume, or may set the electric power value Pa based on the determined tissue volume. If the processor 25 is to set the electric power value Pa based on the parameters, i.e., Ze, Ya, Zmin, α, Pp, etc. and the tissue volume, then the larger the tissue volume of the treatment target, the processor 25 sets the electric power value Pa to a larger value. Similarly, for performing the constant current control process, the processor 25 may set the current value Ia that is a target value to a fixed value TO regardless of the tissue volume, or may set the current value Ia based on the determined tissue volume. If the processor 25 is to set the current value Ia based on the parameters, i.e., Ze, Ya, Zmin, α, Pp, etc. and the tissue volume, then the larger the tissue volume of the treatment target, the processor 25 sets the current value Ia to a larger value.

According to a modification, moreover, the processor 25 switches between the constant voltage control process, the constant power control process, and the constant current control process based on the impedance Z in the sealing phase. In this case, the processor 25 switches between the constant voltage control process, the constant power control process, and the constant current control process based on a switching valve Zs1 and a switching value Zs2 larger than the switching value Zs1. For example, if the impedance Z is smaller than the switching value Zs1, then the processor 25 carries out the constant current control process described hereinbefore on the output from the high-frequency power supply 31. If the impedance Z is equal to or larger than the switching value Zs1 and smaller than the switching value Zs2, then the processor 25 carries out the constant power control process described hereinbefore on the output from the high-frequency power supply 31. If the impedance Z is equal to or larger than the switching value Zs2, then the processor 25 carries out the constant voltage control process described hereinbefore on the output from the high-frequency power supply 31. According to the present modification, the threshold Zth for the impedance Z that is used in determining whether to finish the sealing phase is set to a value larger than the switching values Zs1 and Zs2.

According to the embodiment described hereinbefore, the threshold value Zth that is used in determining whether to finish the sealing phase is of the fixed value Zth0. However, the disclosed technology is not limited to such details. According to a modification, the processor 25 sets the threshold value Zth for the impedance Z based on the parameters described hereinbefore, i.e., Ze, Ya, Zmin, α, Pp, etc. and the tissue volume. In this case, the larger the tissue volume of the treatment target, the processor 25 sets the threshold value Zth to a higher value.

According to a modification, furthermore, a threshold value Yfth for an elapsed time Yf from the start of the sealing phase is set rather than the threshold value Zth for the impedance Z. In this case, the threshold value Yfth for the elapsed time Yf is used in determining whether to finish the sealing phase. The threshold value Yfth for the elapsed time Yf may be a fixed value Yfth0 or may be set based on the parameters described hereinbefore, i.e., Ze, Ya, Zmin, α, Pp, etc. and the tissue volume. If the threshold value Yfth is to be set based on the tissue volume, then the larger the tissue volume of the treatment target, the processor 25 sets the threshold value Yfth to a longer value.

According to the embodiment, etc. hereinabove, when the sealing phase is ended or immediately after the end of the sealing phase, the output from the high-frequency power supply 31 and the output from the heater power supply 41 are stopped by the processing of S104. However, the disclosed technology is not limited to such details. According to a modification, the processor 25 causes the output to the heater 23 to be continued instead of carrying out the processing of S104. In this case, the output from the heater power supply 41 is controlled to be lowered to prevent the treatment target from being modified by the heater heat, for example. According to a modification, furthermore, the output from the heater power supply 41 may be increased to increase the temperature T of the heater 23 from the sealing phase for incising the treatment target with the heater heat. In this case, the temperature T of the heater 23 increases to a temperature higher than 200° C., i.e., in excess of 200° C. In the modification that continues the output to the heater 23 even after the end of the sealing phase, the processor 25 causes the heater power supply 41 to stop the output upon elapse of a certain time from the end of the sealing phase or based on an operation made by the surgeon or the like.

Furthermore, according to a modification, the processor 25 continues the output to the electrodes 21 and 22, instead of performing the processing of S104. In this case, for example, the output from the high-frequency power supply 31 is controlled to reduce the output from the high-frequency power supply 31 in a manner not to modify the treatment target with the high-frequency current. The processor 25 stops the output from the high-frequency power supply 31 upon elapse of a certain time from the end of the sealing phase or based on an operation entered by the surgeon or the like.

According to the embodiment, etc. hereinabove, the energy output source (31, 41) of the energy source apparatus (3) outputs high-frequency electric power (P) to the bipolar electrodes (21, 22) thereby to cause a high-frequency current to flow through the treatment target between the bipolar electrodes (21, 22), and outputs heater electric power (P') to the heater (23) thereby to cause the heater (23) to generate heat. The processor (25) performs control to output the high-frequency electric power (P) to the bipolar electrodes (21 and 22) and detects a parameter (Ze, Ya, Zmin, α, Pp, or the like) that varies depending on the tissue volume of the treatment target and that is related to at least one of the impedance (Z) of the treatment target and the output to the bipolar electrodes (21 and 22). The processor (25) sets a target value (Ta or the like) related to the output control process for controlling the output to the heater (23) based on the detected parameter (Ze, Ya, Zmin, α, Pp, or the like), and controls the output to the heater (23) to modify the treatment target with the heat of the heater (23) based on the set target value (Ta or the like). Then, the smaller the tissue volume of the treatment target, the processor (25) increases the output to the heater (23) and increases the temperature (T) of the heater (23) until at least a predetermined point of time after starting the output control process for controlling the output to the heater (23) based on the set target value (Ta or the like).

The disclosed technology is not limited to the embodiments described hereinbefore, but various modifications may be made therein without departing from the scope of the invention when it is reduced to practice. The embodiments may be appropriately combined as much as possible, and the combinations offer combined advantages. Furthermore, the embodiments include inventions in various stages, and various inventions can be extracted by appropriately combining a plurality of components that are disclosed.

In sum, one aspect of the disclosed technology is directed to an energy source apparatus for use with a treatment tool having a heater and bipolar electrodes. The energy source apparatus includes an energy output source that outputs high-frequency electric power to the bipolar electrodes so as to cause a high-frequency current to flow through a treatment target between the bipolar electrodes and outputs heater electric power to the heater so as to cause the heater to generate heat. A processor controls the output to the bipolar electrodes and the output to the heater. The processor causes the high-frequency electric power to be output to the bipolar electrodes and detects a parameter that varies depending on tissue volume of the treatment target. The parameter is related to (i) impedance of the treatment target and/or (ii) the output to the bipolar electrodes. The processor sets a target value based on the detected parameter and the target value is related to an output control process for controlling the output to the heater. The processor controls the output to the heater based on the target value so as to modify the treatment target with the heat of the heater. With respect to a smaller tissue volume, the processor increases the output to the heater and increases a temperature of the heater until at least a predetermined point of time after starting the output control process for controlling the output to the heater based on the target value.

The processor lowers the output to the heater to lower the temperature of the heater when a duration time of the output control process for controlling the output to the heater has become equal to or greater than a switching value. The processor sets the switching value for the duration time based on the parameter that varies depending on the tissue volume and the smaller the tissue volume, the processor sets the switching value for the duration time to a shorter value. The processor causes the output to the bipolar electrodes continuously so as to modify the treatment target with the high-frequency current applied thereto after starting the output control process for controlling the output to the heater based on the target value. The larger the tissue volume based on the parameter, the processor increases the output to the bipolar electrodes after starting the output control process for controlling the output to the heater based on the target value. The processor sets a first target temperature for the heater as the target value for the output control process for controlling the output to the heater based on the parameter that varies depending on the tissue volume. The processor performs an output control process for causing the heater to reach the first target temperature and maintaining the heater at the first target temperature from the start of the output control process for controlling the output to the heater. And the smaller the tissue volume, the processor sets the first target temperature to a higher value.

The processor lowers the output to the heater to lower the temperature of the heater from the first target temperature so that the duration time of the output control process for controlling the output to the heater has become equal to or greater than a switching value. The processor sets the switching value for the duration time, based on the parameter that varies depending on the tissue volume, and the smaller the tissue volume, the processor sets the switching value for the duration time to a shorter value. The processor switches to an output control process on the output to the heater for causing the heater to reach a second target temperature and maintaining the heater at the second target temperature so that a duration time of the output control process for controlling the output to the heater has become equal to or greater than a switching value. The processor sets the first target temperature to a value higher than the second target temperature if the tissue volume based on the parameter is smaller than a reference value and sets the first target temperature to a value identical to the second target temperature if the tissue volume is equal to or greater than the reference value. The processor sets the second target temperature to a fixed value regardless of the tissue volume.

Another aspect of the disclosed technology is directed to a treatment system having a treatment tool. The treatment tool includes a heater and bipolar electrodes to grip a treatment target. An energy source apparatus is used to supply electrical energy to the treatment tool. The energy output source outputs high-frequency electric power to the bipolar electrodes so as to cause a high-frequency current to flow through a treatment target between the bipolar electrodes and outputs heater electric power to the heater so as to cause the heater to generate heat. A processor controls the output to the respective bipolar electrodes and the heater. The processor causes the high-frequency electric power to be output to the bipolar electrodes and detects a parameter that varies depending on tissue volume of the treatment target. The parameter is related to (i) impedance of the treatment target and/or (ii) the output to the bipolar electrodes. The processor sets a target value based on the detected parameter. The target value is related to an output control process for controlling the output to the heater. The processor controls the output to the heater based on the target value so as to modify the treatment target with the heat of the heater and with respect to a smaller tissue volume, the processor increases the output to the heater and increases a temperature of the heater until at least a predetermined point of time after starting the output control process for controlling the output to the heater based on the target value.

A further aspect of the disclosed technology is directed to a method of operating a treatment system having a treatment tool. The treatment tool includes a heater and bipolar electrodes to grip a treatment target and an energy source apparatus used to supply electrical energy to the treatment tool. The energy output source outputs high-frequency electric power to the bipolar electrodes so as to cause a high-frequency current to flow through a treatment target between the bipolar electrodes and outputs heater electric power to the heater so as to cause the heater to generate heat. The energy source apparatus includes at least one processor to control the output to the bipolar electrodes and the heater, respectively. The at least one processor is causing the high-frequency electric power to be output to the bipolar electrodes and detecting a parameter that varies depending on tissue volume of the treatment target. The parameter is related to (i) impedance of the treatment target and/or (ii) the output to the bipolar electrodes. The processor is setting a target value based on the detected parameter, the target value is related to an output control process for controlling the output to the heater. The processor is controlling the output to the heater based on the target value so as to modify the treatment target with the heat of the heater. With respect to a smaller tissue volume, the processor is increasing the output to the heater and is increasing a temperature of the heater until at least a predetermined point of time after starting the output control process for controlling the output to the heater based on the target value.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An energy source apparatus for use with a treatment tool having a heater and bipolar electrodes, the energy source apparatus comprising:
an energy output source that outputs high-frequency electric power to the bipolar electrodes so as to cause a high-frequency current to flow through a treatment target between the bipolar electrodes, and outputs heater electric power to the heater so as to cause the heater to generate heat; and
a processor controls the output to the bipolar electrodes and the output to the heater, wherein the processor:
causes the high-frequency electric power to be output to the bipolar electrodes and detects a parameter that varies depending on tissue volume of the treatment target and wherein the parameter being related to (i) impedance of the treatment target and/or (ii) the output to the bipolar electrodes;
sets a target value based on the detected parameter, the target value being related to an output control process for controlling the output to the heater; controls the output to the heater based on the target value so as to modify the treatment target with the heat of the heater; and
with respect to a smaller tissue volume, increases the output to the heater and increases a temperature of the heater until at least a predetermined point of time after starting the output control process for controlling the output to the heater based on the target value.

2. The energy source apparatus of claim 1, wherein the processor lowers the output to the heater to lower the temperature of the heater when a duration time of the output control process for controlling the output to the heater has become equal to or greater than a switching value.

3. The energy source apparatus of claim 2, wherein the processor sets the switching value for the duration time based on the parameter that varies depending on the tissue volume, and the smaller the tissue volume, the processor sets the switching value for the duration time to a shorter value.

4. The energy source apparatus of claim 1, wherein the processor causes the output to the bipolar electrodes continuously so as to modify the treatment target with the high-frequency current applied thereto after starting the output control process for controlling the output to the heater based on the target value, and the larger the tissue volume based on the parameter, the processor increases the output to the bipolar electrodes after starting the output control process for controlling the output to the heater based on the target value.

5. The energy source apparatus of claim 1, wherein the processor sets a first target temperature for the heater as the target value for the output control process for controlling the output to the heater based on the parameter that varies depending on the tissue volume, the processor performs an output control process for causing the heater to reach the first target temperature and maintaining the heater at the first target temperature, from the start of the output control process for controlling the output to the heater, and the smaller the tissue volume, the processor sets the first target temperature to a higher value.

6. The energy source apparatus of claim 5, wherein the processor lowers the output to the heater to lower the temperature of the heater from the first target temperature so that the duration time of the output control process for controlling the output to the heater has become equal to or greater than a switching value.

7. The energy source apparatus of claim 6, wherein the processor sets the switching value for the duration time, based on the parameter that varies depending on the tissue volume, and the smaller the tissue volume, the processor sets the switching value for the duration time to a shorter value.

8. The energy source apparatus of claim 5, wherein the processor switches to an output control process on the output to the heater for causing the heater to reach a second target temperature and maintaining the heater at the second target temperature so that a duration time of the output control process for controlling the output to the heater has become equal to or greater than a switching value, and the processor sets the first target temperature to a value higher than the second target temperature if the tissue volume based on the parameter is smaller than a reference value, and sets the first target temperature to a value identical to the second target temperature if the tissue volume is equal to or greater than the reference value.

9. The energy source apparatus of claim 8, wherein the processor sets the second target temperature to a fixed value regardless of the tissue volume.

10. A treatment system comprising:
a treatment tool having a heater and bipolar electrodes to grip a treatment target; and
an energy source apparatus used to supply electrical energy to the treatment tool wherein:
the energy output source outputs high-frequency electric power to the bipolar electrodes so as to cause a high-frequency current to flow through a treatment target between the bipolar electrodes, and outputs heater electric power to the heater so as to cause the heater to generate heat, and
a processor controls the output to the respective bipolar electrodes and the heater, wherein the processor:
causes the high-frequency electric power to be output to the bipolar electrodes and detects a parameter that varies depending on tissue volume of the treatment target and wherein the parameter being related to (i) impedance of the treatment target and/or (ii) the output to the bipolar electrodes;
sets a target value based on the detected parameter, the target value being related to an output control process for controlling the output to the heater;
controls the output to the heater based on the target value so as to modify the treatment target with the heat of the heater; and
with respect to a smaller tissue volume, increases the output to the heater and increases a temperature of the heater until at least a predetermined point of time after starting the output control process for controlling the output to the heater based on the target value.

11. The treatment system of claim 10, wherein the processor lowers the output to the heater to lower the temperature of the heater when a duration time of the output control process for controlling the output to the heater has become equal to or greater than a switching value.

12. The treatment system of claim 10, wherein the processor causes the output to the bipolar electrodes continuously so as to modify the treatment target with the high-frequency current applied thereto and subsequently to the start of the output control process for controlling the output to the heater, and the larger the tissue volume based on the parameter, the processor increases the output to the bipolar electrodes and subsequently to the start of the output control process for controlling the output to the heater based on the target value.

13. The treatment system of claim 10, wherein the processor sets a first target temperature for the heater as the target value for the output control process for controlling the output to the heater based on the parameter that varies depending on the tissue volume, the processor performs an output control process for causing the heater to reach the first target temperature and maintaining the heater at the first target temperature, from the start of the output control process for controlling the output to the heater, and the smaller the tissue volume, the processor sets the first target temperature to a higher value.

14. A method of operating a treatment system having a treatment tool including a heater and bipolar electrodes to grip a treatment target and an energy source apparatus used to supply electrical energy to the treatment tool, the energy output source outputs high-frequency electric power to the bipolar electrodes so as to cause a high-frequency current to flow through a treatment target between the bipolar electrodes, and outputs heater electric power to the heater so as to cause the heater to generate heat, the energy source apparatus comprising at least one processor to control the output to the bipolar electrodes and the heater, respectively, wherein the at least one processor:
causes the high-frequency electric power to be output to the bipolar electrodes and detecting a parameter that varies depending on tissue volume of the treatment target and wherein the parameter being related to (i) impedance of the treatment target and/or (ii) the output to the bipolar electrodes;
sets a target value based on the detected parameter, the target value being related to an output control process for controlling the output to the heater;
controls the output to the heater based on the target value so as to modify the treatment target with the heat of the heater; and
with respect to a smaller tissue volume, increases the output to the heater and increasing a temperature of the heater until at least a predetermined point of time after starting the output control process for controlling the output to the heater based on the target value.

* * * * *